United States Patent [19]
Ertl et al.

[11] Patent Number: 5,698,202
[45] Date of Patent: Dec. 16, 1997

[54] REPLICATION-DEFECTIVE ADENOVIRUS HUMAN TYPE 5 RECOMBINANT AS A RABIES VACCINE CARRIER

[75] Inventors: Hildegund C. J. Ertl, Villanova; James M. Wilson, Gladwyne, both of Pa.

[73] Assignees: The Wistar Institute of Anatomy & Biology; The Trustees of the University of Pennsylvania, both of Philadelphia, Pa.

[21] Appl. No.: 461,837

[22] Filed: Jun. 5, 1995

[51] Int. Cl.$^6$ ............... A61K 39/12; A61K 39/205; C12N 15/00; C12N 7/00
[52] U.S. Cl. ............... 424/199.1; 424/224.1; 424/233.1; 435/235.1; 435/320.1; 935/32; 935/34; 935/57; 935/65
[58] Field of Search ............... 424/199.1, 224.1, 424/233.1; 935/32, 34, 57, 65; 435/235.1, 320.1

[56] References Cited

U.S. PATENT DOCUMENTS 4,393,201  7/1983  Curtis et al. ............... 536/23.72

FOREIGN PATENT DOCUMENTS

| WO93/19191 | 9/1993 | WIPO. |
| WO94/12649 | 6/1994 | WIPO. |
| WO94/26914 | 11/1994 | WIPO. |
| WO94/28152 | 12/1994 | WIPO. |
| WO94/28938 | 12/1994 | WIPO. |
| WO95/00655 | 1/1995 | WIPO. |
| WO95/02697 | 1/1995 | WIPO. |

OTHER PUBLICATIONS

Levrevo, M. et al, 1990, Gene, pp. 195–202.

K. Charlton et al, "Oral Rabies Vaccination of Skunks and Foxes with a Recombinant Human Adenovirus Vaccine", *Arch. Virol.*, 123:169–179 (1992).

D. Johnson et al, "Abundant Expression of Herpes Simplex Virus Glycoprotein gb Using an Adenovirus Vector", *Virology*, 164:1–14 (1988).

R. Dewar et al, "Synthesis and Processing of Human Immunodeficiency Virus type 1 Envelope Proteins Encoded by a Recombinant Human Adenovirus", *J. Virol.*, 63(1):129–136 (Jan., 1989).

B. Brochier et al, "Towards Rabies Elimination in Belgium by Fox Vaccination Using a Vaccinia–Rabies Glycoprotein Recombinant Virus", *Vaccine*, 12(15):1368–1371 (Nov., 1994).

L. Prevec et al, "A Recombinant Human Adenovirus Vaccine Against Rabies", *J. Infect. Dis.*, 161:27–30 (Jan., 1990).

K. Kozarsky et al, "In Vivo Correction of Low Density Lipoprotein Receptor Deficiency in the Watanabe Heritable Hyperlipidemic Rabbit with Recombinant Adenoviruses", *J. Biol. Chem.*, 269(18):13695–13702 (May 6, 1994) [Kozarsky I].

K. Kozarsky et al, "Adenovirus–Mediated Correction of the Genetic Defect in Hepatocytes from Patients with Familial Hypercholesterolemia", *Somatic Cell and Molecular Genetics*, 19(5):449–458 (Sep., 1993) [Kozarsky II].

K. Kozarsky et al, "Gene Therapy: Adenovirus Vectors", *Curr. Opin. Genet. Devel.*, 3:499–503 (Mar., 1993) [Kozarsky III].

Y. Yang et al, "MHC Class I–Restricted Cytotoxic T Lymphocytes to Viral Antigens Destroy Hepatocytes in Mice Infected with E1–Deleted Recombinant Adenoviruses", *Immunity*, 1:433–442 (Aug., 1994) [Yang I].

Y. Yang et al, "Cellular Immunity to Viral Antigens Limits E1–Deleted Adenoviruses for Gene Therapy", *Proc. Natl. Acad. Sci. USA*, 91:4407–4411 (May, 1994) [Yang II].

Y. Yang et al, "Inactivation of E2a in Recombinant Adenoviruses Improves the Prospect for Gene Therapy in Cystic Fibrosis", *Nature Genetics*, 7:362–369 (Jul., 1994) [Yang III].

S. Ishibashi et al, "Hypercholesterolemia in Low Density Lipoprotein Receptor Knockout Mice and its Reversal by Adenovirus–Mediated Gene Delivery", *J. Clin. Invest.*, 92:883–893 (Aug., 1993).

J. Engelhardt et al, "Ablation of E2A in Recombinant Adenoviruses Improves Transgene Persistence and Decreases Inflammatory Response in Mouse Liver", *Proc. Natl. Acad. Sci. USA*, 91:6196–6200 (Jun., 1994) [Engelhardt I].

J. Engelhardt et al, "Adenovirus–Mediated Transfer of the CFTR Gene to Lung of Nonhuman Primates: Biological Efficacy Study", *Human Genet. Ther.*, 4:759–769 (Dec., 1993) [Engelhardt II].

J. Engelhardt et al, "Prolonged Transgene Expression in Cotton Rat Lung with Recombinant Adenoviruses Defective in E2a", *Human Gene Ther.*, 5:1217–1229 (Oct., 1994) [Engelhardt III].

M Horwitz, "Adenoviridae and Their Replication", *Virology*, 2d edition, ed. B. N. Fields, Raven Press, Ltd., New York, Chapter 60, pp. 1679–1721 (1990).

M. Boshart et al, "A Very Strong Enhancer is Located Upstream of an Immediate Early Gene of Human Cytomegalovirus", *Cell*, 41:521–530 (Jun., 1985).

K. Fisher et al, "Biochemical and Functional Analysis of an Adenovirus–Based Ligand Complex for Gene Transfer", *Biochem. J.*, 299:49–58 (Apr. 1, 1994).

(List continued on next page.)

*Primary Examiner*—Marian C. Knode
*Assistant Examiner*—Ali R. Salimi
*Attorney, Agent, or Firm*—Howson and Howson

[57] ABSTRACT

A method of vaccinating a human or animal against rabies is provided by administering a replication defective recombinant adenovirus containing a complete deletion of its E1 gene and at least a partial deletion of its E3 gene, said virus containing in the site of the E1 deletion a sequence comprising a non-adenovirus promoter directing the replication and expression of DNA encoding a rabies virus G protein, which, when administered to the animal or human in said recombinant virus, elicits a substantially complete protective immune response against rabies virus.

11 Claims, 13 Drawing Sheets

OTHER PUBLICATIONS

T. Shenk et al, "Genetic Analysis of Adenoviruses", *Current Topics in Microbiol. and Immunol.*, 111:1–39 (1984).

M. Rosenfeld et al, "In Vivo Transfer of the Human Cystic Fibrosis Transmembrane Conductance Regulator Gene to the Airway Epithelium", *Cell*, 68:143–155 (Jan. 10, 1992).

J. Logan et al, "Adenovirus Tripartite Leader Sequence Enhances Translation of mRNAs Late After Infection", *Proc. Natl. Acad. Sci. USA*, 81:3655–3659 (Jun., 1984).

P. Van Der Vliet et al, "Thermolabile DNA Binding Proteins from Cells Infected with a Temperature–Sensitive Mutant of Adenovirus Defective in Viral DNA Synthesis", *J. Virol.*, 15(2):348–354 (Feb., 1975).

M. Eloit et al, "Construction of a Defective Adenovirus Vector Expressing the Pseudorabies Virus Glycoprotein gp50 and its Use as a Live Vaccine", *J. Gen. Virol.*, 71(10):2425–2431 (Oct., 1990).

S. Jacobs et al, "High–Level Expression of the Tick–Borne Encephalitis Virus NS1 Protein by Using an Adenovirus––based Vector: Protection Elicited in a Murine Model", *J. Virol.*, 66:2086–2095 (Apr., 1992).

T. Ragot et al, "Replication–Defective Recombinant Adenovirus Expressing the Epstein–Barr Virus (EBV) Envelope Glycoprotein gp340/220 Induces Protective Immunity Against EBV–induced Lymphomas in the Cottontop Tamarin", *J. Gen. Virol.*, 74(3):501–507 (Mar., 1993).

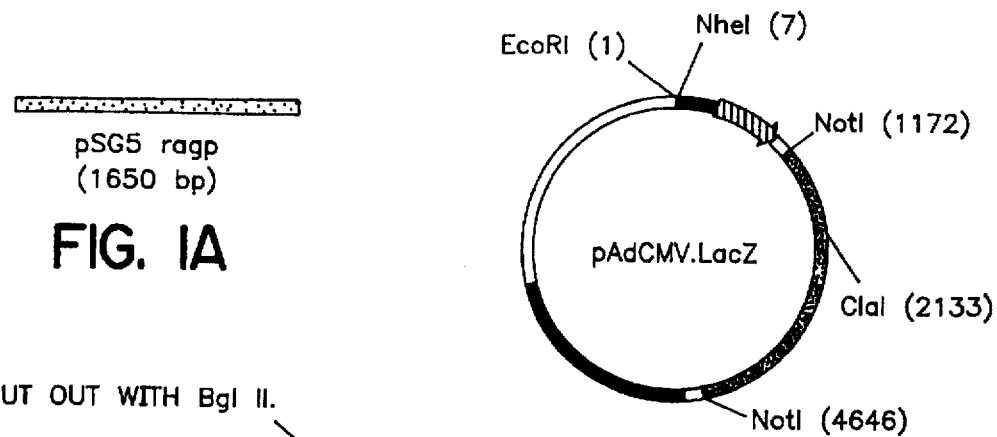
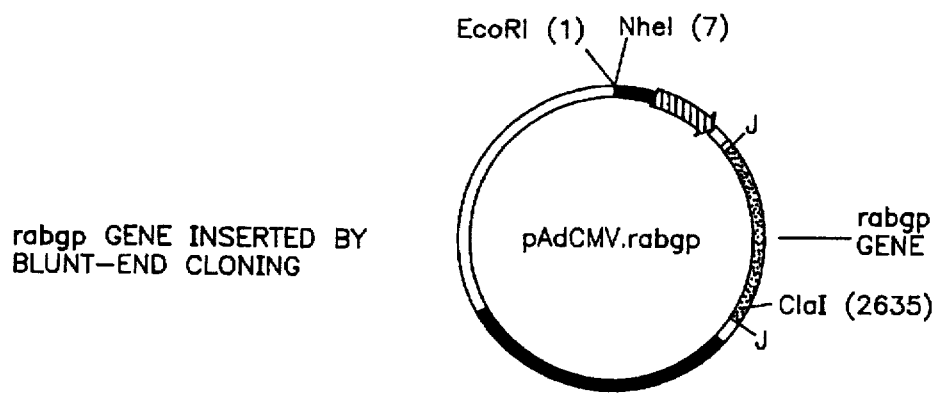
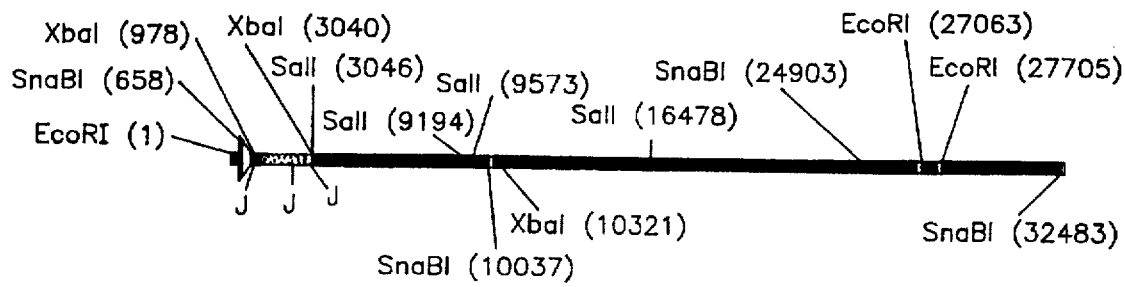

FIGURE 2A

| | | | | | |
|---|---|---|---|---|---|
| GAATTCGCTA | GCATCATCAA | TAATATACCT | TATTTTGGAT | TGAAGCCAAT | 50 |
| ATGATAATGA | GGGGGTGGAG | TTTGTGACGT | GGCGCGGGGC | GTGGGAACGG | 100 |
| GGCGGGTGAC | GTAGTAGTGT | GGCGGAAGTG | TGATGTTGCA | AGTGTGGCGG | 150 |
| AACACATGTA | AGCGACGGAT | GTGGCAAAAG | TGACGTTTTT | GGTGTGCGCC | 200 |
| GGTGTACACA | GGAAGTGACA | ATTTTCGCGC | GGTTTTAGGC | GGATGTTGTA | 250 |
| GTAAATTTGG | GCGTAACCGA | GTAAGATTTG | GCCATTTTCG | CGGGAAAACT | 300 |
| GAATAAGAGG | AAGTGAAATC | TGAATAATTT | TGTGTTACTC | ATAGCGCGTA | 350 |
| ATATTTGTCT | AGGGAGATCA | GCCTGCAGGT | CGTTACATAA | CTTACGGTAA | 400 |
| ATGGCCCGCC | TGGCTGACCG | CCCAACGACC | CCGCCCATT | GACGTCAATA | 450 |
| ATGACGTATG | TTCCATAGT | AACGCCAATA | GGGACTTTCC | ATTGACGTCA | 500 |
| ATGGGTGGAG | TATTTACGGT | AAACTGCCCA | CTTGGCAGTA | CATCAAGTGT | 550 |
| ATCATATGCC | AAGTACGCCC | CCTATTGACG | TCAATGACGG | TAAATGGCCC | 600 |
| GCCTGGCATT | ATGCCCAGTA | CATGACCTTA | TGGGACTTTC | CTACTTGGCA | 650 |
| GTACATCTAC | GTATTAGTCA | TCGCTATTAC | CATGGTGATG | CGGTTTTGGC | 700 |
| AGTACATCAA | TGGGCGTGGA | TAGCGGTTTG | ACTCACGGGG | ATTTCCAAGT | 750 |
| CTCCACCCCA | TTGACGTCAA | TGGGAGTTTG | TTTTGGCACC | AAAATCAACG | 800 |
| GGACTTTCCA | AAATGTCGTA | ACAACTCCGC | CCCATTGACG | CAAATGGGCG | 850 |
| GTAGGCGTGT | ACGGTGGGAG | GTCTATATAA | GCAGAGCTCG | TTTAGTGAAC | 900 |
| CGTCAGATCG | CCTGGAGACG | CCATCCACGC | TGTTTTGACC | TCCATAGAAG | 950 |
| ACACCGGGAC | CGATCCAGCC | TCCGGACTCT | AGAGGATCCG | GTACTCGAGG | 1000 |
| AACTGAAAAA | CCAGAAAGTT | AACTGGTAAG | TTTAGTCTTT | TTGTCTTTTA | 1050 |
| TTTCAGGTCC | CGGATCCGGT | GGTGGTGCAA | ATCAAAGAAC | TGCTCCTCAG | 1100 |
| TGGATGTTGC | CTTTACTTCT | AGGCCTGTAC | GGAAGTGTTA | CTTCTGCTCT | 1150 |
| AAAAGCTGCG | GAATTGTACC | CGCGGCCAGG | AAAG ATG GTT CCT CAG | | 1196 |
| | | | Met Val Pro Gln | | |
| | | | 1 | | |
| GCT CTC CTG TTT GTA CCC CTT CTG GTT TTT CCA TTG TGT TTT | | | | | 1238 |
| Ala Leu Leu Phe Val Pro Leu Leu Val Phe Pro Leu Cys Phe | | | | | |
| 5 | | 10 | | 15 | |

FIGURE 2B

| GGG | AAA | TTC | CCT | ATT | TAC | ACG | ATA | CTA | GAC | AAG | CTT | GGT | CCC | 1280 |
| Gly | Lys | Phe | Pro | Ile | Tyr | Thr | Ile | Leu | Asp | Lys | Leu | Gly | Pro | |
| | 20 | | | | | 25 | | | | | 30 | | | |

| TGG | AGC | CCG | ATT | GAC | ATA | CAT | CAC | CTC | AGC | TGC | CCA | AAC | AAT | 1322 |
| Trp | Ser | Pro | Ile | Asp | Ile | His | His | Leu | Ser | Cys | Pro | Asn | Asn | |
| | | 35 | | | | | 40 | | | | | 45 | | |

| TTG | GTA | GTG | GAG | GAC | GAA | GGA | TGC | ACC | AAC | CTG | TCA | GGG | TTC | 1364 |
| Leu | Val | Val | Glu | Asp | Glu | Gly | Cys | Thr | Asn | Leu | Ser | Gly | Phe | |
| | | | | 50 | | | | | 55 | | | | 60 | |

| TCC | TAC | ATG | GAA | CTT | AAA | GTT | GGA | TAC | ATC | TTA | GCC | ATA | AAA | 1406 |
| Ser | Tyr | Met | Glu | Leu | Lys | Val | Gly | Tyr | Ile | Leu | Ala | Ile | Lys | |
| | | | | | 65 | | | | | 70 | | | | |

| ATG | AAC | GGG | TTC | ACT | TGC | ACA | GGC | GTT | GTG | ACG | GAG | GCT | GAA | 1448 |
| Met | Asn | Gly | Phe | Thr | Cys | Thr | Gly | Val | Val | Thr | Glu | Ala | Glu | |
| 75 | | | | | 80 | | | | | 85 | | | | |

| ACC | TAC | ACT | AAC | TTC | GTT | GGT | TAT | GTC | ACA | ACC | ACG | TTC | AAA | 1490 |
| Thr | Tyr | Thr | Asn | Phe | Val | Gly | Tyr | Val | Thr | Thr | Thr | Phe | Lys | |
| | | 90 | | | | | 95 | | | | | 100 | | |

| AGA | AAG | CAT | TTC | CGC | CCA | ACA | CCA | GAT | GCA | TGT | AGA | GCC | GCG | 1532 |
| Arg | Lys | His | Phe | Arg | Pro | Thr | Pro | Asp | Ala | Cys | Arg | Ala | Ala | |
| | | | 105 | | | | | 110 | | | | | 115 | |

| TAC | AAC | TGG | AAG | ATG | GCC | GGT | GAC | CCC | AGA | TAT | GAA | GAG | TCT | 1574 |
| Tyr | Asn | Trp | Lys | Met | Ala | Gly | Asp | Pro | Arg | Tyr | Glu | Glu | Ser | |
| | | | | 120 | | | | | 125 | | | | 130 | |

| CTA | CAC | AAT | CCG | TAC | CCT | GAC | TAC | CGC | TGG | CTT | CGA | ACT | GTA | 1616 |
| Leu | His | Asn | Pro | Tyr | Pro | Asp | Tyr | Arg | Trp | Leu | Arg | Thr | Val | |
| | | | | 135 | | | | | 140 | | | | | |

| AAA | ACC | ACC | AAG | GAG | TCT | CTC | GTT | ATC | ATA | TCT | CCA | AGT | GTA | 1658 |
| Lys | Thr | Thr | Lys | Glu | Ser | Leu | Val | Ile | Ile | Ser | Pro | Ser | Val | |
| 145 | | | | | 150 | | | | | 155 | | | | |

| GCA | GAT | TTG | GAC | CCA | TAT | GAC | AGA | TCC | CTT | CAC | TCG | AGG | GTC | 1700 |
| Ala | Asp | Leu | Asp | Pro | Tyr | Asp | Arg | Ser | Leu | His | Ser | Arg | Val | |
| | | 160 | | | | | 165 | | | | | 170 | | |

| TTC | CCT | AGC | GGG | AAG | TGC | TCA | GGA | GTA | GCG | GTG | TCT | TCT | ACC | 1742 |
| Phe | Pro | Ser | Gly | Lys | Cys | Ser | Gly | Val | Ala | Val | Ser | Ser | Thr | |
| | | | 175 | | | | | 180 | | | | | 185 | |

| TAC | TGC | TCC | ACT | AAC | CAC | GAT | TAC | ACC | ATT | TGG | ATG | CCC | GAG | 1784 |
| Tyr | Cys | Ser | Thr | Asn | His | Asp | Tyr | Thr | Ile | Trp | Met | Pro | Glu | |
| | | | | 190 | | | | | 195 | | | | 200 | |

FIGURE 2C

| | |
|---|---|
| AAT CCG AGA CTA GGG ATG TCT TGT GAC ATT TTT ACC AAT AGT<br>Asn Pro Arg Leu Gly Met Ser Cys Asp Ile Phe Thr Asn Ser<br>                          205                      210 | 1826 |
| AGA GGG AAG AGA GCA TCC AAA GGG AGT GAG ACT TGC GGC TTT<br>Arg Gly Lys Arg Ala Ser Lys Gly Ser Glu Thr Cys Gly Phe<br>215                    220                  225 | 1868 |
| GTA GAT GAA AGA GGC CTA TAT AAG TCT TTA AAA GGA GCA TGC<br>Val Asp Glu Arg Gly Leu Tyr Lys Ser Leu Lys Gly Ala Cys<br>    230                      235                240 | 1910 |
| AAA CTC AAG TTA TGT GGA GTT CTA GGA CTT AGA CTT ATG GAT<br>Lys Leu Lys Leu Cys Gly Val Leu Gly Leu Arg Leu Met Asp<br>       245                  250              255 | 1952 |
| GGA ACA TGG GTC GCG ATG CAA ACA TCA AAT GAA ACC AAA TGG<br>Gly Thr Trp Val Ala Met Gln Thr Ser Asn Glu Thr Lys Trp<br>          260                  265              270 | 1994 |
| TGC CCT CCC GAT CAG TTG GTG AAC CTG CAC GAC TTT CGC TCA<br>Cys Pro Pro Asp Gln Leu Val Asn Leu His Asp Phe Arg Ser<br>              275                  280 | 2036 |
| GAC GAA ATT GAG CAC CTT GTT GTA GAG GAG TTG GTC AGG AAG<br>Asp Glu Ile Glu His Leu Val Val Glu Glu Leu Val Arg Lys<br>285                    290                  295 | 2078 |
| AGA GAG GAG TGT CTG GAT GCA CTA GAG TCC ATC ATG ACA ACC<br>Arg Glu Glu Cys Leu Asp Ala Leu Glu Ser Ile Met Thr Thr<br>    300                      305              310 | 2120 |
| AAG TCA GTG AGT TTC AGA CGT CTC AGT CAT TTA AGA AAA CTT<br>Lys Ser Val Ser Phe Arg Arg Leu Ser His Leu Arg Lys Leu<br>       315                  320              325 | 2162 |
| GTC CCT GGG TTT GGA AAA GCA TAT ACC ATA TTC AAC AAG ACC<br>Val Pro Gly Phe Gly Lys Ala Tyr Thr Ile Phe Asn Lys Thr<br>          330                  335              340 | 2204 |
| TTG ATG GAA GCC GAT GCT CAC TAC AAG TCA GTC AGA ACT TGG<br>Leu Met Glu Ala Asp Ala His Tyr Lys Ser Val Arg Thr Trp<br>              345                  350 | 2246 |
| AAT GAG ATC CTC CCT TCA AAA GGG TGT TTA AGA GTT GGG GGG<br>Asn Glu Ile Leu Pro Ser Lys Gly Cys Leu Arg Val Gly Gly<br>355                    360                  365 | 2288 |
| AGG TGT CAT CCT CAT GTG AAC GGG GTG TTT TTC AAT GGT ATA<br>Arg Cys His Pro His Val Asn Gly Val Phe Phe Asn Gly Ile<br>    370                      375              380 | 2330 |

FIGURE 2D

| | | | | | | | | | | | | |
|---|---|---|---|---|---|---|---|---|---|---|---|---|
| ATA | TTA | GGA | CCT | GAC | GGC | AAT | GTC | TTA | ATC | CCA | GAG | ATG | CAA | 2372
| Ile | Leu | Gly | Pro | Asp | Gly | Asn | Val | Leu | Ile | Pro | Glu | Met | Gln |
| | | 385 | | | | | 390 | | | | | 395 | |

```
ATA TTA GGA CCT GAC GGC AAT GTC TTA ATC CCA GAG ATG CAA    2372
Ile Leu Gly Pro Asp Gly Asn Val Leu Ile Pro Glu Met Gln
        385                 390                 395

TCA TCC CTC CTC CAG CAA CAT ATG GAG TTG TTG GAA TCC TCG    2414
Ser Ser Leu Leu Gln Gln His Met Glu Leu Leu Glu Ser Ser
            400                 405                 410

GTT ATC CCC CTT GTG CAC CCC CTG GCA GAC CCG TCT ACC GTT    2456
Val Ile Pro Leu Val His Pro Leu Ala Asp Pro Ser Thr Val
                415                 420

TTC AAG GAC GGT GAC GAG GCT GAG GAT TTT GTT GAA GTT CAC    2498
Phe Lys Asp Gly Asp Glu Ala Glu Asp Phe Val Glu Val His
425                 430                 435

CTT CCC GAT GTG CAC AAT CAG GTC TCA GGA GTT GAC TTG GGT    2540
Leu Pro Asp Val His Asn Gln Val Ser Gly Val Asp Leu Gly
    440                 445                 450

CTC CCG AAC TGG GGG AAG TAT GTA TTA CTG AGT GCA GGG GCC    2582
Leu Pro Asn Trp Gly Lys Tyr Val Leu Leu Ser Ala Gly Ala
        455                 460                 465

CTG ACT GCC TTG ATG TTG ATA ATT TTC CTG ATG ACA TGT TGT    2624
Leu Thr Ala Leu Met Leu Ile Ile Phe Leu Met Thr Cys Cys
            470                 475                 480

AGA AGA GTC AAT CGA TCA GAA CCT ACG CAA CAC AAT CTC AGA    2666
Arg Arg Val Asn Arg Ser Glu Pro Thr Gln His Asn Leu Arg
                485                 490

GGG ACA GGG AGG GAG GTG TCA GTC ACT CCC CAA AGC GGG AAG    2708
Gly Thr Gly Arg Glu Val Ser Val Thr Pro Gln Ser Gly Lys
495                 500                 505

ATC ATA TCT TCA TGG GAA TCA CAC AAG AGT GGG GGT GAG ACC    2750
Ile Ile Ser Ser Trp Glu Ser His Lys Ser Gly Gly Glu Thr
    510                 515                 520

AGA CTG TGAGGACTGG CCGTCCTTTC AACGATCCAA GTCCTGAAGA        2796
Arg Leu

TCACCTCCCC TTGGGGGGTT CTTTTTAAAA AGGCCGCGGG GATCCAGACA     2846

TGATAAGATA CATTGATGAG TTTGGACAAA CCACAACTAG AATGCAGTGA     2896

AAAAAATGCT TTATTTGTGA AATTTGTGAT GCTATTGCTT TATTTGTAAC     2946

CATTATAAGC TGCAATAAAC AAGTTAACAA CAACAATTGC ATTCATTTTA     2996

TGTTTCAGGT TCAGGGGGAG GTGTGGGAGG TTTTTTCGGA TCCTCTAGAG     3046

TCGACCTGCA GGCTGATCTG GAAGGTGCTG AGGTACGATG AGACCCGCAC     3096
```

FIGURE 2E

```
CAGGTGCAGA CCCTGCGAGT GTGGCGGTAA ACATATTAGG AACCAGCCTG    3146
TGATGCTGGA TGTGACCGAG GAGCTGAGGC CCGATCACTT GGTGCTGGCC    3196
TGCACCCGCG CTGAGTTTGG CTCTAGCGAT GAAGATACAG ATTGAGGTAC    3246
TGAAATGTGT GGGCGTGGCT TAAGGGTGGG AAAGAATATA TAAGGTGGGG    3296
GTCTTATGTA GTTTTGTATC TGTTTTGCAG CAGCCGCCGC CGCCATGAGC    3346
ACCAACTCGT TTGATGGAAG CATTGTGAGC TCATATTTGA CAACGCGCAT    3396
GCCCCCATGG GCCGGGGTGC GTCAGAATGT GATGGGCTCC AGCATTGATG    3446
GTCGCCCCGT CCTGCCCGCA AACTCTACTA CCTTGACCTA CGAGACCGTG    3496
TCTGGAACGC CGTTGGAGAC TGCAGCCTCC GCCGCCGCTT CAGCCGCTGC    3546
AGCCACCGCC CGCGGGATTG TGACTGACTT TGCTTTCCTG AGCCCGCTTG    3596
CAAGCAGTGC AGCTTCCCGT TCATCCGCCC GCGATGACAA GTTGACGGCT    3646
CTTTTGGCAC AATTGGATTC TTTGACCCGG GAACTTAATG TCGTTTCTCA    3696
GCAGCTGTTG GATCTGCGCC AGCAGGTTTC TGCCCTGAAG GCTTCCTCCC    3746
CTCCCAATGC GGTTTAAAAC ATAAATAAAA AACCAGACTC TGTTTGGATT    3796
TGGATCAAGC AAGTGTCTTG CTGTCTTTAT TTAGGGGTTT TGCGCGCGCG    3846
GTAGGCCCGG GACCAGCGGT CTCGGTCGTT GAGGGTCCTG TGTATTTTTT    3896
CCAGGACGTG GTAAAGGTGA CTCTGGATGT TCAGATACAT GGGCATAAGC    3946
CCGTCTCTGG GGTGGAGGTA GCACCACTGC AGAGCTTCAT GCTGCGGGT     3996
GGTGTTGTAG ATGATCCAGT CGTAGCAGGA GCGCTGGGCG TGGTGCCTAA    4046
AAATGTCTTT CAGTAGCAAG CTGATTGCCA GGGGCAGGCC CTTGGTGTAA    4096
GTGTTTACAA AGCGGTTAAG CTGGGATGGG TGCATACGTG GGGATATGAG    4146
ATGCATCTTG GACTGTATTT TTAGGTTGGC TATGTTCCCA GCCATATCCC    4196
TCCGGGGATT CATGTTGTGC AGAACCACCA GCACAGTGTA TCCGGTGCAC    4246
TTGGGAAATT TGTCATGTAG CTTAGAAGGA AATGCGTGGA AGAACTTGGA    4296
GACGCCCTTG TGACCTCCAA GATTTTCCAT GCATTCGTCC ATAATGATGG    4346
CAATGGGCCC ACGGCGGCG  GCCTGGGCGA AGATATTTCT GGGATCACTA    4396
ACGTCATAGT TGTGTTCCAG GATGAGATCG TCATAGGCCA TTTTTACAAA    4446
```

FIGURE 2F

```
GCGCGGGCGG AGGGTGCCAG ACTGCGGTAT AATGGTTCCA TCCGGCCCAG    4496
GGGCGTAGTT ACCCTCACAG ATTTGCATTT CCCACGCTTT GAGTTCAGAT    4546
GGGGGGATCA TGTCTACCTG CGGGGCGATG AAGAAACGG  TTTCCGGGGT    4596
AGGGAGATC  AGCTGGGAAG AAAGCAGGTT CCTGAGCAGC TGCGACTTAC    4646
CGCAGCCGGT GGGCCCGTAA ATCACACCTA TTACCGGGTG CAACTGGTAG    4696
TTAAGAGAGC TGCAGCTGCC GTCATCCCTG AGCAGGGGGG CCACTTCGTT    4746
AAGCATGTCC CTGACTCGCA TGTTTTCCCT GACCAAATCC GCCAGAAGGC    4796
GCTCGCCGCC CAGCGATAGC AGTTCTTGCA AGGAAGCAAA GTTTTTCAAC    4846
GGTTTGAGAC CGTCCGCCGT AGGCATGCTT TTGAGCGTTT GACCAAGCAG    4896
TTCCAGGCGG TCCCACAGCT CGGTCACCTG CTCTACGGCA TCTCGATCCA    4946
GCATATCTCC TCGTTTCGCG GGTTGGGGCG GCTTTCGCTG TACGGCAGTA    4996
GTCGGTGCTC GTCCAGACGG GCCAGGGTCA TGTCTTTCCA CGGGCGCAGG    5046
GTCCTCGTCA GCGTAGTCTG GGTCACGGTG AAGGGGTGCG CTCCGGGCTG    5096
CGCGCTGGCC AGGGTGCGCT TGAGGCTGGT CCTGCTGGTG CTGAAGCGCT    5146
GCCGGTCTTC GCCCTGCGCG TCGGCCAGGT AGCATTTGAC CATGGTGTCA    5196
TAGTCCAGCC CCTCCGCGGC GTGGCCCTTG GCGCGCAGCT TGCCCTTGGA    5246
GGAGGCGCCG CACGAGGGC  AGTGCAGACT TTTGAGGGCG TAGAGCTTGG    5296
GCGCGAGAAA TACCGATTCC GGGGAGTAGG CATCCGCGCC GCAGGCCCCG    5346
CAGACGGTCT CGCATTCCAC GAGCCAGGTG AGCTCTGGCC GTTCGGGTC    5396
AAAAACCAGG TTTCCCCCAT GCTTTTTGAT GCGTTTCTTA CCTCTGGTTT    5446
CCATGAGCCG GTGTCCACGC TCGGTGACGA AAAGGCTGTC CGTGTCCCCG    5496
TATACAGACT TGAGAGGCCT GTCCTCGACC GATGCCCTTG AGAGCCTTCA    5546
ACCCAGTCAG CTCCTTCCGG TGGGCGCGGG GCATGACTAT CGTCGCCGCA    5596
CTTATGACTG TCTTCTTTAT CATGCAACTC GTAGGACAGG TGCCGGCAGC    5646
GCTCTGGGTC ATTTTCGGCG AGGACCGCTT TCGCTGGAGC GCGACGATGA    5696
TCGGCCTGTC GCTTGCGGTA TTCGGAATCT TGCACGCCCT CGCTCAAGCC    5746
TTCGTCACTG GTCCCGCCAC CAAACGTTTC GGCGAGAAGC AGGCCATTAT    5796
```

FIGURE 2G

| | | | | | |
|---|---|---|---|---|---|
| CGCCGGCATG | GCGGCCGACG | CGCTGGGCTA | CGTCTTGCTG | GCGTTCGCGA | 5846 |
| CGCGAGGCTG | GATGGCCTTC | CCCATTATGA | TTCTTCTCGC | TTCCGGCGGC | 5896 |
| ATCGGGATGC | CCGCGTTGCA | GGCCATGCTG | TCCAGGCAGG | TAGATGACGA | 5946 |
| CCATCAGGGA | CAGCTTCAAG | GATCGCTCGC | GGCTCTTACC | AGCCTAACTT | 5996 |
| CGATCACTGG | ACCGCTGATC | GTCACGGCGA | TTTATGCCGC | CTCGGCGAGC | 6046 |
| ACATGGAACG | GGTTGGCATG | GATTGTAGGC | GCCGCCCTAT | ACCTTGTCTG | 6096 |
| CCTCCCCGCG | TTGCGTCGCG | GTGCATGGAG | CCGGGCCACC | TCGACCTGAA | 6146 |
| TGGAAGCCGG | CGGCACCTCG | CTAACGGATT | CACCACTCCA | AGAATTGGAG | 6196 |
| CCAATCAATT | CTTGCGGAGA | ACTGTGAATG | CGCAAACCAA | CCCTTGGCAG | 6246 |
| AACATATCCA | TCGCGTCCGC | CATCTCCAGC | AGCCGCACGC | GGCGCATCTC | 6296 |
| GGGCAGCGTT | GGGTCCTGGC | CACGGGTGCG | CATGATCGTG | CTCCTGTCGT | 6346 |
| TGAGGACCCG | GCTAGGCTGG | CGGGGTTGCC | TTACTGGTTA | GCAGAATGAA | 6396 |
| TCACCGATAC | GCGAGCGAAC | GTGAAGCGAC | TGCTGCTGCA | AAACGTCTGC | 6446 |
| GACCTGAGCA | ACAACATGAA | TGGTCTTCGG | TTTCCGTGTT | TCGTAAAGTC | 6496 |
| TGGAAACGCG | GAAGTCAGCG | CCCTGCACCA | TTATGTTCCG | GATCTGCATC | 6546 |
| GCAGGATGCT | GCTGGCTACC | CTGTGGAACA | CCTACATCTG | TATTAACGAA | 6596 |
| GCCTTTCTCA | ATGCTCACGC | TGTAGGTATC | TCAGTTCGGT | GTAGGTCGTT | 6646 |
| CGCTCCAAGC | TGGGCTGTGT | GCACGAACCC | CCCGTTCAGC | CCGACCGCTG | 6696 |
| CGCCTTATCC | GGTAACTATC | GTCTTGAGTC | CAACCCGGTA | AGACACGACT | 6746 |
| TATCGCCACT | GGCAGCAGCC | ACTGGTAACA | GGATTAGCAG | AGCGAGGTAT | 6796 |
| GTAGGCGGTG | CTACAGAGTT | CTTGAAGTGG | TGGCCTAACT | ACGGCTACAC | 6846 |
| TAGAAGGACA | GTATTTGGTA | TCTGCGCTCT | GCTGAAGCCA | GTTACCTTCG | 6896 |
| GAAAAGAGT | TGGTAGCTCT | TGATCCGGCA | ACAAACCAC | CGCTGGTAGC | 6946 |
| GGTGGTTTTT | TTGTTTGCAA | GCAGCAGATT | ACGCGCAGAA | AAAAGGATC | 6996 |
| TCAAGAAGAT | CCTTTGATCT | TTTCTACGGG | GTCTGACGCT | CAGTGGAACG | 7046 |
| AAAACTCACG | TTAAGGGATT | TTGGTCATGA | GATTATCAAA | AAGGATCTTC | 7096 |
| ACCTAGATCC | TTTTAAATTA | AAAATGAAGT | TTTAAATCAA | TCTAAAGTAT | 7146 |

FIGURE 2H

```
ATATGAGTAA ACTTGGTCTG ACAGTTACCA ATGCTTAATC AGTGAGGCAC    7196
CTATCTCAGC GATCTGTCTA TTTCGTTCAT CCATAGTTGC CTGACTCCCC    7246
GTCGTGTAGA TAACTACGAT ACGGGAGGGC TTACCATCTG GCCCCAGTGC    7296
TGCAATGATA CCGCGAGACC CACGCTCACC GGCTCCAGAT TTATCAGCAA    7346
TAAACCAGCC AGCCGGAAGG GCCGAGCGCA GAAGTGGTCC TGCAACTTTA    7396
TCCGCCTCCA TCCAGTCTAT TAATTGTTGC CGGGAAGCTA GAGTAAGTAG    7446
TTCGCCAGTT AATAGTTTGC GCAACGTTGT TGCCATTGCT GCAGGCATCG    7496
TGGTGTCACG CTCGTCGTTT GGTATGGCTT CATTCAGCTC CGGTTCCCAA    7546
CGATCAAGGC GAGTTACATG ATCCCCCATG TTGTGCAAAA AAGCGGTTAG    7596
CTCCTTCGGT CCTCCGATCG TTGTCAGAAG TAAGTTGGCC GCAGTGTTAT    7646
CACTCATGGT TATGGCAGCA CTGCATAATT CTCTTACTGT CATGCCATCC    7696
GTAAGATGCT TTTCTGTGAC TGGTGAGTAC TCAACCAAGT CATTCTGAGA    7746
ATAGTGTATG CGGCGACCGA GTTGCTCTTG CCCGGCGTCA ACACGGGATA    7796
ATACCGCGCC ACATAGCAGA ACTTTAAAAG TGCTCATCAT TGGAAAACGT    7846
TCTTCGGGGC GAAAACTCTC AAGGATCTTA CCGCTGTTGA GATCCAGTTC    7896
GATGTAACCC ACTCGTGCAC CCAACTGATC TTCAGCATCT TTTACTTTCA    7946
CCAGCGTTTC TGGGTGAGCA AAAACAGGAA GGCAAAATGC CGCAAAAAAG    7996
GGAATAAGGG CGACACGGAA ATGTTGAATA CTCATACTCT TCCTTTTTCA    8046
ATATTATTGA AGCATTTATC AGGGTTATTG TCTCATGAGC GGATACATAT    8096
TTGAATGTAT TTAGAAAAAT AAACAAATAG GGGTTCCGCG CACATTTCCC    8146
CGAAAAGTGC CACCTGACGT CTAAGAAACC ATTATTATCA TGACATTAAC    8196
CTATAAAAAT AGGCGTATCA CGAGGCCCTT TCGTCTTCAA               8236
```

5,698,202

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
       ( A ) LENGTH: 8236 base pairs
       ( B ) TYPE: nucleic acid
       ( C ) STRANDEDNESS: double
       ( D ) TOPOLOGY: Not Relevant ( i i ) MOLECULE TYPE: cDNA ( i x ) FEATURE:
       ( A ) NAME/KEY: CDS
       ( B ) LOCATION: 1185..2756

( x i ) SEQUENCE DESCRIPTION: SEQ ID NO:1:

```
GAATTCGCTA  GCATCATCAA  TAATATACCT  TATTTTGGAT  TGAAGCCAAT  ATGATAATGA      60

GGGGGTGGAG  TTTGTGACGT  GGCGCGGGGC  GTGGGAACGG  GGCGGGTGAC  GTAGTAGTGT     120

GGCGGAAGTG  TGATGTTGCA  AGTGTGGCGG  AACACATGTA  AGCGACGGAT  GTGGCAAAAG     180

TGACGTTTTT  GGTGTGCGCC  GGTGTACACA  GGAAGTGACA  ATTTTCGCGC  GGTTTTAGGC     240

GGATGTTGTA  GTAAATTTGG  GCGTAACCGA  GTAAGATTTG  GCCATTTTCG  CGGGAAAACT     300
```

-continued

```
GAATAAGAGG AAGTGAAATC TGAATAATTT TGTGTTACTC ATAGCGCGTA ATATTTGTCT    360
AGGGAGATCA GCCTGCAGGT CGTTACATAA CTTACGGTAA ATGGCCCGCC TGGCTGACCG    420
CCCAACGACC CCCGCCCATT GACGTCAATA ATGACGTATG TTCCCATAGT AACGCCAATA    480
GGGACTTTCC ATTGACGTCA ATGGGTGGAG TATTTACGGT AAACTGCCCA CTTGGCAGTA    540
CATCAAGTGT ATCATATGCC AAGTACGCCC CCTATTGACG TCAATGACGG TAAATGGCCC    600
GCCTGGCATT ATGCCCAGTA CATGACCTTA TGGGACTTTC CTACTTGGCA GTACATCTAC    660
GTATTAGTCA TCGCTATTAC CATGGTGATG CGGTTTTGGC AGTACATCAA TGGGCGTGGA    720
TAGCGGTTTG ACTCACGGGG ATTTCCAAGT CTCCACCCCA TTGACGTCAA TGGGAGTTTG    780
TTTTGGCACC AAAATCAACG GGACTTTCCA AATGTCGTA ACAACTCCGC CCCATTGACG    840
CAAATGGGCG GTAGGCGTGT ACGGTGGGAG GTCTATATAA GCAGAGCTCG TTTAGTGAAC    900
CGTCAGATCG CCTGGAGACG CCATCCACGC TGTTTGACC TCCATAGAAG ACACCGGGAC    960
CGATCCAGCC TCCGGACTCT AGAGGATCCG GTACTCGAGG AACTGAAAAA CCAGAAAGTT   1020
AACTGGTAAG TTTAGTCTTT TTGTCTTTTA TTTCAGGTCC CGGATCCGGT GGTGGTGCAA   1080
ATCAAAGAAC TGCTCCTCAG TGGATGTTGC CTTTACTTCT AGGCCTGTAC GGAAGTGTTA   1140
CTTCTGCTCT AAAAGCTGCG GAATTGTACC CGCGGCCAGG AAAG ATG GTT CCT CAG   1196
                                                     Met Val Pro Gln
                                                     1
GCT CTC CTG TTT GTA CCC CTT CTG GTT TTT CCA TTG TGT TTT GGG AAA   1244
Ala Leu Leu Phe Val Pro Leu Leu Val Phe Pro Leu Cys Phe Gly Lys
 5              10                 15                  20
TTC CCT ATT TAC ACG ATA CTA GAC AAG CTT GGT CCC TGG AGC CCG ATT   1292
Phe Pro Ile Tyr Thr Ile Leu Asp Lys Leu Gly Pro Trp Ser Pro Ile
         25                 30                  35
GAC ATA CAT CAC CTC AGC TGC CCA AAC AAT TTG GTA GTG GAG GAC GAA   1340
Asp Ile His His Leu Ser Cys Pro Asn Asn Leu Val Val Glu Asp Glu
             40                 45                  50
GGA TGC ACC AAC CTG TCA GGG TTC TCC TAC ATG GAA CTT AAA GTT GGA   1388
Gly Cys Thr Asn Leu Ser Gly Phe Ser Tyr Met Glu Leu Lys Val Gly
         55                 60                  65
TAC ATC TTA GCC ATA AAA ATG AAC GGG TTC ACT TGC ACA GGC GTT GTG   1436
Tyr Ile Leu Ala Ile Lys Met Asn Gly Phe Thr Cys Thr Gly Val Val
 70                 75                  80
ACG GAG GCT GAA ACC TAC ACT AAC TTC GTT GGT TAT GTC ACA ACC ACG   1484
Thr Glu Ala Glu Thr Tyr Thr Asn Phe Val Gly Tyr Val Thr Thr Thr
 85             90                  95                  100
TTC AAA AGA AAG CAT TTC CGC CCA ACA CCA GAT GCA TGT AGA GCC GCG   1532
Phe Lys Arg Lys His Phe Arg Pro Thr Pro Asp Ala Cys Arg Ala Ala
            105                 110                 115
TAC AAC TGG AAG ATG GCC GGT GAC CCC AGA TAT GAA GAG TCT CTA CAC   1580
Tyr Asn Trp Lys Met Ala Gly Asp Pro Arg Tyr Glu Glu Ser Leu His
        120                 125                 130
AAT CCG TAC CCT GAC TAC CGC TGG CTT CGA ACT GTA AAA ACC ACC AAG   1628
Asn Pro Tyr Pro Asp Tyr Arg Trp Leu Arg Thr Val Lys Thr Thr Lys
            135                 140                 145
GAG TCT CTC GTT ATC ATA TCT CCA AGT GTA GCA GAT TTG GAC CCA TAT   1676
Glu Ser Leu Val Ile Ile Ser Pro Ser Val Ala Asp Leu Asp Pro Tyr
150                 155                 160
GAC AGA TCC CTT CAC TCG AGG GTC TTC CCT AGC GGG AAG TGC TCA GGA   1724
Asp Arg Ser Leu His Ser Arg Val Phe Pro Ser Gly Lys Cys Ser Gly
165                 170                 175                 180
GTA GCG GTG TCT TCT ACC TAC TGC TCC ACT AAC CAC GAT TAC ACC ATT   1772
Val Ala Val Ser Ser Thr Tyr Cys Ser Thr Asn His Asp Tyr Thr Ile
                185                 190                 195
```

| | |
|---|---|
| TGG ATG CCC GAG AAT CCG AGA CTA GGG ATG TCT TGT GAC ATT TTT ACC<br>Trp Met Pro Glu Asn Pro Arg Leu Gly Met Ser Cys Asp Ile Phe Thr<br>200                        205                        210 | 1820 |
| AAT AGT AGA GGG AAG AGA GCA TCC AAA GGG AGT GAG ACT TGC GGC TTT<br>Asn Ser Arg Gly Lys Arg Ala Ser Lys Gly Ser Glu Thr Cys Gly Phe<br>215                        220                        225 | 1868 |
| GTA GAT GAA AGA GGC CTA TAT AAG TCT TTA AAA GGA GCA TGC AAA CTC<br>Val Asp Glu Arg Gly Leu Tyr Lys Ser Leu Lys Gly Ala Cys Lys Leu<br>230                        235                        240 | 1916 |
| AAG TTA TGT GGA GTT CTA GGA CTT AGA CTT ATG GAT GGA ACA TGG GTC<br>Lys Leu Cys Gly Val Leu Gly Leu Arg Leu Met Asp Gly Thr Trp Val<br>245                        250                        255                        260 | 1964 |
| GCG ATG CAA ACA TCA AAT GAA ACC AAA TGG TGC CCT CCC GAT CAG TTG<br>Ala Met Gln Thr Ser Asn Glu Thr Lys Trp Cys Pro Pro Asp Gln Leu<br>265                        270                        275 | 2012 |
| GTG AAC CTG CAC GAC TTT CGC TCA GAC GAA ATT GAG CAC CTT GTT GTA<br>Val Asn Leu His Asp Phe Arg Ser Asp Glu Ile Glu His Leu Val Val<br>280                        285                        290 | 2060 |
| GAG GAG TTG GTC AGG AAG AGA GAG GAG TGT CTG GAT GCA CTA GAG TCC<br>Glu Glu Leu Val Arg Lys Arg Glu Glu Cys Leu Asp Ala Leu Glu Ser<br>295                        300                        305 | 2108 |
| ATC ATG ACA ACC AAG TCA GTG AGT TTC AGA CGT CTC AGT CAT TTA AGA<br>Ile Met Thr Thr Lys Ser Val Ser Phe Arg Arg Leu Ser His Leu Arg<br>310                        315                        320 | 2156 |
| AAA CTT GTC CCT GGG TTT GGA AAA GCA TAT ACC ATA TTC AAC AAG ACC<br>Lys Leu Val Pro Gly Phe Gly Lys Ala Tyr Thr Ile Phe Asn Lys Thr<br>325                        330                        335                        340 | 2204 |
| TTG ATG GAA GCC GAT GCT CAC TAC AAG TCA GTC AGA ACT TGG AAT GAG<br>Leu Met Glu Ala Asp Ala His Tyr Lys Ser Val Arg Thr Trp Asn Glu<br>345                        350                        355 | 2252 |
| ATC CTC CCT TCA AAA GGG TGT TTA AGA GTT GGG GGA AGG TGT CAT CCT<br>Ile Leu Pro Ser Lys Gly Cys Leu Arg Val Gly Gly Arg Cys His Pro<br>360                        365                        370 | 2300 |
| CAT GTG AAC GGG GTG TTT TTC AAT GGT ATA ATA TTA GGA CCT GAC GGC<br>His Val Asn Gly Val Phe Phe Asn Gly Ile Ile Leu Gly Pro Asp Gly<br>375                        380                        385 | 2348 |
| AAT GTC TTA ATC CCA GAG ATG CAA TCA TCC CTC CTC CAG CAA CAT ATG<br>Asn Val Leu Ile Pro Glu Met Gln Ser Ser Leu Leu Gln Gln His Met<br>390                        395                        400 | 2396 |
| GAG TTG TTG GAA TCC TCG GTT ATC CCC CTT GTG CAC CCC CTG GCA GAC<br>Glu Leu Leu Glu Ser Ser Val Ile Pro Leu Val His Pro Leu Ala Asp<br>405                        410                        415                        420 | 2444 |
| CCG TCT ACC GTT TTC AAG GAC GGT GAC GAG GCT GAG GAT TTT GTT GAA<br>Pro Ser Thr Val Phe Lys Asp Gly Asp Glu Ala Glu Asp Phe Val Glu<br>                        425                        430                        435 | 2492 |
| GTT CAC CTT CCC GAT GTG CAC AAT CAG GTC TCA GGA GTT GAC TTG GGT<br>Val His Leu Pro Asp Val His Asn Gln Val Ser Gly Val Asp Leu Gly<br>                    440                        445                        450 | 2540 |
| CTC CCG AAC TGG GGG AAG TAT GTA TTA CTG AGT GCA GGG GCC CTG ACT<br>Leu Pro Asn Trp Gly Lys Tyr Val Leu Leu Ser Ala Gly Ala Leu Thr<br>                    455                        460                        465 | 2588 |
| GCC TTG ATG TTG ATA ATT TTC CTG ATG ACA TGT TGT AGA AGA GTC AAT<br>Ala Leu Met Leu Ile Ile Phe Leu Met Thr Cys Cys Arg Arg Val Asn<br>470                        475                        480 | 2636 |
| CGA TCA GAA CCT ACG CAA CAC AAT CTC AGA GGG ACA GGG AGG GAG GTG<br>Arg Ser Glu Pro Thr Gln His Asn Leu Arg Gly Thr Gly Arg Glu Val<br>485                        490                        495                        500 | 2684 |
| TCA GTC ACT CCC CAA AGC GGG AAG ATC ATA TCT TCA TGG GAA TCA CAC<br>Ser Val Thr Pro Gln Ser Gly Lys Ile Ile Ser Ser Trp Glu Ser His<br>                    505                        510                        515 | 2732 |

```
AAG AGT GGG GGT GAG ACC AGA CTG TGAGGACTGG CCGTCCTTTC AACGATCCAA       2786
Lys Ser Gly Gly Glu Thr Arg Leu
                520

GTCCTGAAGA TCACCTCCCC TTGGGGGGTT CTTTTTAAAA AGGCCGCGGG GATCCAGACA      2846
TGATAAGATA CATTGATGAG TTTGGACAAA CCACAACTAG AATGCAGTGA AAAAAATGCT      2906
TTATTTGTGA AATTTGTGAT GCTATTGCTT TATTTGTAAC CATTATAAGC TGCAATAAAC      2966
AAGTTAACAA CAACAATTGC ATTCATTTTA TGTTTCAGGT TCAGGGGGAG GTGTGGGAGG      3026
TTTTTTCGGA TCCTCTAGAG TCGACCTGCA GGCTGATCTG GAAGGTGCTG AGGTACGATG      3086
AGACCCGCAC CAGGTGCAGA CCCTGCGAGT GTGGCGGTAA ACATATTAGG AACCAGCCTG      3146
TGATGCTGGA TGTGACCGAG GAGCTGAGGC CCGATCACTT GGTGCTGGCC TGCACCCGCG      3206
CTGAGTTTGG CTCTAGCGAT GAAGATACAG ATTGAGGTAC TGAAATGTGT GGGCGTGGCT      3266
TAAGGGTGGG AAAGAATATA TAAGGTGGGG GTCTTATGTA GTTTGTATC TGTTTTGCAG       3326
CAGCCGCCGC CGCCATGAGC ACCAACTCGT TGATGGAAG CATTGTGAGC TCATATTTGA       3386
CAACGCGCAT GCCCCATGG GCCGGGGTGC GTCAGAATGT GATGGGCTCC AGCATTGATG       3446
GTCGCCCCGT CCTGCCCGCA AACTCTACTA CCTTGACCTA CGAGACCGTG TCTGGAACGC      3506
CGTTGGAGAC TGCAGCCTCC GCCGCCGCTT CAGCCGCTGC AGCCACCGCC CGCGGGATTG      3566
TGACTGACTT TGCTTTCCTG AGCCCGCTTG CAAGCAGTGC AGCTTCCCGT TCATCCGCCC      3626
GCGATGACAA GTTGACGGCT CTTTTGGCAC AATTGGATTC TTTGACCCGG GAACTTAATG      3686
TCGTTTCTCA GCAGCTGTTG GATCTGCGCC AGCAGGTTTC TGCCCTGAAG GCTTCCTCCC      3746
CTCCCAATGC GGTTTAAAAC ATAAATAAAA AACCAGACTC TGTTTGGATT TGGATCAAGC      3806
AAGTGTCTTG CTGTCTTTAT TTAGGGGTTT TGCGCGCGCG GTAGGCCCGG GACCAGCGGT      3866
CTCGGTCGTT GAGGGTCCTG TGTATTTTTT CCAGGACGTG GTAAAGGTGA CTCTGGATGT      3926
TCAGATACAT GGGCATAAGC CCGTCTCTGG GGTGGAGGTA GCACCACTGC AGAGCTTCAT      3986
GCTGCGGGGT GGTGTTGTAG ATGATCCAGT CGTAGCAGGA GCGCTGGGCG TGGTGCCTAA      4046
AAATGTCTTT CAGTAGCAAG CTGATTGCCA GGGGCAGGCC CTTGGTGTAA GTGTTTACAA      4106
AGCGGTTAAG CTGGATGGG TGCATACGTG GGGATATGAG ATGCATCTTG GACTGTATTT       4166
TTAGGTTGGC TATGTTCCCA GCCATATCCC TCCGGGGATT CATGTTGTGC AGAACCACCA      4226
GCACAGTGTA TCCGGTGCAC TTGGGAAATT TGTCATGTAG CTTAGAAGGA AATGCGTGGA      4286
AGAACTTGGA GACGCCCTTG TGACCTCCAA GATTTTCCAT GCATTCGTCC ATAATGATGG      4346
CAATGGGCCC ACGGGCGGCG GCCTGGGCGA AGATATTTCT GGGATCACTA ACGTCATAGT      4406
TGTGTTCCAG GATGAGATCG TCATAGGCCA TTTTTACAAA GCGCGGGCGG AGGGTGCCAG      4466
ACTGCGGTAT AATGGTTCCA TCCGGCCCAG GGGCGTAGTT ACCCTCACAG ATTTGCATTT      4526
CCCACGCTTT GAGTTCAGAT GGGGGATCA TGTCTACCTG CGGGCGATG AAGAAACGG        4586
TTTCCGGGGT AGGGGAGATC AGCTGGAAG AAAGCAGGTT CCTGAGCAGC TGCGACTTAC      4646
CGCAGCCGGT GGGCCCGTAA ATCACACCTA TTACCGGGTG CAACTGGTAG TTAAGAGAGC     4706
TGCAGCTGCC GTCATCCCTG AGCAGGGGGG CCACTTCGTT AAGCATGTCC CTGACTCGCA     4766
TGTTTTCCCT GACCAAATCC GCCAGAAGGC GCTCGCCGCC CAGCGATAGC AGTTCTTGCA    4826
AGGAAGCAAA GTTTTTCAAC GGTTTGAGAC CGTCCGCCGT AGGCATGCTT TTGAGCGTTT     4886
GACCAAGCAG TTCCAGGCGG TCCCACAGCT CGGTCACCTG CTCTACGGCA TCTCGATCCA     4946
GCATATCTCC TCGTTTCGCG GGTTGGGGCG GCTTTCGCTG TACGGCAGTA GTCGGTGCTC     5006
GTCCAGACGG GCCAGGGTCA TGTCTTTCCA CGGGCGCAGG GTCCTCGTCA GCGTAGTCTG     5066
```

```
GGTCACGGTG AAGGGGTGCG CTCCGGGCTG CGCGCTGGCC AGGGTGCGCT TGAGGCTGGT    5126
CCTGCTGGTG CTGAAGCGCT GCCGGTCTTC GCCCTGCGCG TCGGCCAGGT AGCATTTGAC    5186
CATGGTGTCA TAGTCCAGCC CCTCCGCGGC GTGGCCCTTG GCGCGCAGCT TGCCCTTGGA    5246
GGAGGCGCCG CACGAGGGGC AGTGCAGACT TTTGAGGGCG TAGAGCTTGG GCGCGAGAAA    5306
TACCGATTCC GGGGAGTAGG CATCCGCGCC GCAGGCCCCG CAGACGGTCT CGCATTCCAC    5366
GAGCCAGGTG AGCTCTGGCC GTTCGGGGTC AAAAACCAGG TTTCCCCCAT GCTTTTTGAT    5426
GCGTTTCTTA CCTCTGGTTT CCATGAGCCG GTGTCCACGC TCGGTGACGA AAAGGCTGTC    5486
CGTGTCCCCG TATACAGACT TGAGAGGCCT GTCCTCGACC GATGCCCTTG AGAGCCTTCA    5546
ACCCAGTCAG CTCCTTCCGG TGGGCGCGGG GCATGACTAT CGTCGCCGCA CTTATGACTG    5606
TCTTCTTTAT CATGCAACTC GTAGGACAGG TGCCGGCAGC GCTCTGGGTC ATTTTCGGCG    5666
AGGACCGCTT TCGCTGGAGC GCGACGATGA TCGGCCTGTC GCTTGCGGTA TTCGGAATCT    5726
TGCACGCCCT CGCTCAAGCC TTCGTCACTG GTCCCGCCAC CAAACGTTTC GGCGAGAAGC    5786
AGGCCATTAT CGCCGGCATG GCGGCCGACG CGCTGGGCTA CGTCTTGCTG GCGTTCGCGA    5846
CGCGAGGCTG GATGGCCTTC CCCATTATGA TTCTTCTCGC TTCCGGCGGC ATCGGGATGC    5906
CCGCGTTGCA GGCCATGCTG TCCAGGCAGG TAGATGACGA CCATCAGGGA CAGCTTCAAG    5966
GATCGCTCGC GGCTCTTACC AGCCTAACTT CGATCACTGG ACCGCTGATC GTCACGGCGA    6026
TTTATGCCGC CTCGGCGAGC ACATGGAACG GGTTGGCATG GATTGTAGGC GCCGCCCTAT    6086
ACCTTGTCTG CCTCCCCGCG TTGCGTCGCG GTGCATGGAG CCGGGCCACC TCGACCTGAA    6146
TGGAAGCCGG CGGCACCTCG CTAACGGATT CACCACTCCA AGAATTGGAG CCAATCAATT    6206
CTTGCGGAGA ACTGTGAATG CGCAAACCAA CCCTTGGCAG AACATATCCA TCGCGTCCGC    6266
CATCTCCAGC AGCCGCACGC GGCGCATCTC GGGCAGCGTT GGTCCTGGC CACGGGTGCG    6326
CATGATCGTG CTCCTGTCGT TGAGGACCCG GCTAGGCTGG CGGGGTTGCC TTACTGGTTA    6386
GCAGAATGAA TCACCGATAC GCGAGCGAAC GTGAAGCGAC TGCTGCTGCA AAACGTCTGC    6446
GACCTGAGCA ACAACATGAA TGGTCTTCGG TTTCCGTGTT TCGTAAAGTC TGGAAACGCG    6506
GAAGTCAGCG CCCTGCACCA TTATGTTCCG GATCTGCATC GCAGGATGCT GCTGGCTACC    6566
CTGTGGAACA CCTACATCTG TATTAACGAA GCCTTTCTCA ATGCTCACGC TGTAGGTATC    6626
TCAGTTCGGT GTAGGTCGTT CGCTCCAAGC TGGGCTGTGT GCACGAACCC CCCGTTCAGC    6686
CCGACCGCTG CGCCTTATCC GGTAACTATC GTCTTGAGTC CAACCCGGTA AGACACGACT    6746
TATCGCCACT GGCAGCAGCC ACTGGTAACA GGATTAGCAG AGCGAGGTAT GTAGGCGGTG    6806
CTACAGAGTT CTTGAAGTGG TGGCCTAACT ACGGCTACAC TAGAAGGACA GTATTTGGTA    6866
TCTGCGCTCT GCTGAAGCCA GTTACCTTCG GAAAAAGAGT GGTAGCTCT TGATCCGGCA    6926
AACAAACCAC CGCTGGTAGC GGTGGTTTTT TTGTTTGCAA GCAGCAGATT ACGCGCAGAA    6986
AAAAGGATC TCAAGAAGAT CCTTTGATCT TTTCTACGGG GTCTGACGCT CAGTGGAACG    7046
AAAACTCACG TTAAGGGATT TTGGTCATGA GATTATCAAA AAGGATCTTC ACCTAGATCC    7106
TTTTAAATTA AAAATGAAGT TTAAATCAA TCTAAAGTAT ATATGAGTAA ACTTGGTCTG    7166
ACAGTTACCA ATGCTTAATC AGTGAGGCAC CTATCTCAGC GATCTGTCTA TTTCGTTCAT    7226
CCATAGTTGC CTGACTCCCC GTCGTGTAGA TAACTACGAT ACGGGAGGGC TTACCATCTG    7286
GCCCCAGTGC TGCAATGATA CCGCGAGACC CACGCTCACC GGCTCCAGAT TTATCAGCAA    7346
TAAACCAGCC AGCCGGAAGG GCCGAGCGCA GAAGTGGTCC TGCAACTTTA TCCGCCTCCA    7406
TCCAGTCTAT TAATTGTTGC CGGGAAGCTA GAGTAAGTAG TTCGCCAGTT AATAGTTTGC    7466
```

```
GCAACGTTGT TGCCATTGCT GCAGGCATCG TGGTGTCACG CTCGTCGTTT GGTATGGCTT   7526

CATTCAGCTC CGGTTCCCAA CGATCAAGGC GAGTTACATG ATCCCCATG  TTGTGCAAAA   7586

AAGCGGTTAG CTCCTTCGGT CCTCCGATCG TTGTCAGAAG TAAGTTGGCC GCAGTGTTAT   7646

CACTCATGGT TATGGCAGCA CTGCATAATT CTCTTACTGT CATGCCATCC GTAAGATGCT   7706

TTTCTGTGAC TGGTGAGTAC TCAACCAAGT CATTCTGAGA ATAGTGTATG CGGCGACCGA   7766

GTTGCTCTTG CCCGGCGTCA ACACGGGATA ATACCGCGCC ACATAGCAGA ACTTTAAAAG   7826

TGCTCATCAT TGGAAAACGT TCTTCGGGGC GAAAACTCTC AAGGATCTTA CCGCTGTTGA   7886

GATCCAGTTC GATGTAACCC ACTCGTGCAC CCAACTGATC TTCAGCATCT TTTACTTTCA   7946

CCAGCGTTTC TGGGTGAGCA AAAACAGGAA GGCAAAATGC CGCAAAAAAG GGAATAAGGG   8006

CGACACGGAA ATGTTGAATA CTCATACTCT TCCTTTTTCA ATATTATTGA AGCATTTATC   8066

AGGGTTATTG TCTCATGAGC GGATACATAT TTGAATGTAT TTAGAAAAAT AAACAAATAG   8126

GGGTTCCGCG CACATTTCCC CGAAAAGTGC CACCTGACGT CTAAGAAACC ATTATTATCA   8186

TGACATTAAC CTATAAAAAT AGGCGTATCA CGAGGCCCTT TCGTCTTCAA              8236
```

( 2 ) INFORMATION FOR SEQ ID NO:2:

( i ) SEQUENCE CHARACTERISTICS:
        ( A ) LENGTH: 524 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Val Pro Gln Ala Leu Leu Phe Val Pro Leu Leu Val Phe Pro Leu
 1               5                  10                  15

Cys Phe Gly Lys Phe Pro Ile Tyr Thr Ile Leu Asp Lys Leu Gly Pro
                20                  25                  30

Trp Ser Pro Ile Asp Ile His His Leu Ser Cys Pro Asn Asn Leu Val
            35                  40                  45

Val Glu Asp Glu Gly Cys Thr Asn Leu Ser Gly Phe Ser Tyr Met Glu
        50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr Arg Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220
```

| | | | | | | | | | | | | | | |
|---|---|---|---|---|---|---|---|---|---|---|---|---|---|---|
| Thr 225 | Cys | Gly | Phe | Val | Asp 230 | Glu | Arg | Gly | Leu | Tyr 235 | Lys | Ser | Leu | Lys | Gly 240 |
| Ala | Cys | Lys | Leu | Lys 245 | Leu | Cys | Gly | Val | Leu 250 | Gly | Leu | Arg | Leu | Met 255 | Asp |
| Gly | Thr | Trp | Val 260 | Ala | Met | Gln | Thr | Ser 265 | Asn | Glu | Thr | Lys | Trp 270 | Cys | Pro |
| Pro | Asp | Gln 275 | Leu | Val | Asn | Leu | His 280 | Asp | Phe | Arg | Ser | Asp 285 | Glu | Ile | Glu |
| His | Leu 290 | Val | Val | Glu | Glu | Leu 295 | Val | Arg | Lys | Arg | Glu 300 | Glu | Cys | Leu | Asp |
| Ala 305 | Leu | Glu | Ser | Ile | Met 310 | Thr | Thr | Lys | Ser | Val 315 | Ser | Phe | Arg | Arg | Leu 320 |
| Ser | His | Leu | Arg | Lys 325 | Leu | Val | Pro | Gly | Phe 330 | Gly | Lys | Ala | Tyr | Thr 335 | Ile |
| Phe | Asn | Lys | Thr 340 | Leu | Met | Glu | Ala | Asp 345 | Ala | His | Tyr | Lys | Ser 350 | Val | Arg |
| Thr | Trp | Asn 355 | Glu | Ile | Leu | Pro | Ser 360 | Lys | Gly | Cys | Leu | Arg 365 | Val | Gly | Gly |
| Arg | Cys 370 | His | Pro | His | Val | Asn 375 | Gly | Val | Phe | Phe | Asn 380 | Gly | Ile | Ile | Leu |
| Gly 385 | Pro | Asp | Gly | Asn | Val 390 | Leu | Ile | Pro | Glu | Met 395 | Gln | Ser | Ser | Leu | Leu 400 |
| Gln | Gln | His | Met | Glu 405 | Leu | Leu | Glu | Ser | Ser 410 | Val | Ile | Pro | Leu | Val 415 | His |
| Pro | Leu | Ala | Asp 420 | Pro | Ser | Thr | Val | Phe 425 | Lys | Asp | Gly | Asp | Glu 430 | Ala | Glu |
| Asp | Phe | Val 435 | Glu | Val | His | Leu | Pro 440 | Asp | Val | His | Asn | Gln 445 | Val | Ser | Gly |
| Val | Asp 450 | Leu | Gly | Leu | Pro | Asn 455 | Trp | Gly | Lys | Tyr | Val 460 | Leu | Leu | Ser | Ala |
| Gly 465 | Ala | Leu | Thr | Ala | Leu 470 | Met | Leu | Ile | Ile | Phe 475 | Leu | Met | Thr | Cys | Cys 480 |
| Arg | Arg | Val | Asn | Arg 485 | Ser | Glu | Pro | Thr | Gln 490 | His | Asn | Leu | Arg | Gly 495 | Thr |
| Gly | Arg | Glu | Val 500 | Ser | Val | Thr | Pro | Gln 505 | Ser | Gly | Lys | Ile | Ile 510 | Ser | Ser |
| Trp | Glu | Ser 515 | His | Lys | Ser | Gly | Gly 520 | Glu | Thr | Arg | Leu | | | | |

REPLICATION-DEFECTIVE ADENOVIRUS HUMAN TYPE 5 RECOMBINANT AS A RABIES VACCINE CARRIER

This invention was supported by the National Institutes of Health Grant Nos. NIH AI 33683-02 and NIH AI 27435-05. The United States government has certain rights in this invention.

FIELD OF THE INVENTION

This invention relates generally to recombinant adenoviruses as vaccine components, and more particularly, to the use of a replication deficient adenovirus as a rabies vaccine which induces a protective immune response in a mammalian vaccinate.

BACKGROUND OF THE INVENTION

A replication competent, recombinant adenovirus (Ad) is an adenovirus with intact or functional essential genes, (i.e., E1a, E1b, E2a, E2b and E4). Such recombinant viruses containing a variety of inserted genes have been used as vaccine compositions with some success [see, e.g. Davis, U.S. Pat. No. 4,920,209].

One of these recombinant adenoviruses expressing the rabies G protein was shown to induce protective immunity in animals upon challenge with rabies virus [L. Prevac, J. Infect. Dis., 161:27–30 (1990)]. However, doses above $10^6$ plaque-forming units (pfu) of this replication-competent virus were required to induce complete protection to viral challenge. Further, the use of these viruses in a live form capable of replicating in vivo is an undesirable attribute of a vaccine component.

In contrast, adenoviruses which have been made replication deficient by deletion of the Ad E1a and E1b genes have been used primarily for gene therapy protocols [See, e.g., Kozarsky and Wilson, Curr. Opin. Genet. Dev., 3:499–503 91993); Kozarsky et al, Som. Cell Mol. Genet., 19:449–458 (1993); see also, International Patent Application No. WO95/00655, published Jan. 5, 1995]. Such recombinant, replication deficient adenoviruses have been found to induce cell-mediated immune responses [Y. Yang et al, Proc. Natl. Acad. Sci. USA, 91:4407 (1994) and Y. Yang et al, Immunity, 1:433–442 (August 1994)] and neutralizing antibodies [T. Smith et al, Gene Therapy, 5:397 (1993); K. Kozarsky et al, J. Biol. Chem., 269:13695 (1994)]. None of these articles relating to the use of recombinant replication deficient Ad in gene therapy have measured the induction of a protective immune response.

Others have described the insertion of a foreign gene into a replication-defective adenovirus for putative use as a vaccine [See, e.g.T. Ragot et al, J. Gen. Virol., 74:501–507 (1993); M. Eliot et al, J. Gen. Virol., 71:2425–2431 (1990); and S. C. Jacobs et al, J. Virol., 66:2086–2095 (1992)]. Jacobs et al, cited above, describes a recombinant E1-deleted, E3 intact, Ad containing encephalitis virus protein NS1 under the control of a heterologous cytomegalovirus (CMV) promoter. When mice were immunized with the recombinant Ad vaccines and challenged with virus, Jacobs et al obtained only partial protection (at most a 75% protection) for an average survival of 15 days. Eliot et al, cited above, describe a recombinant E1-deleted, partially E3-deleted Ad with pseudorabies glycoprotein 50 inserted into the E1 deletion site under the control of a homologous Ad promoter. In rabbits and mice, after immunization and challenge, only partial protection was obtained (i.e., about one-third). Ragot et al, cited above, describe a recombinant E1-deleted, partially E3-deleted Ad with Epstein Barr virus glycoprotein gp340/220 inserted into the E1 deletion site under the control of a homologous Ad promoter. In marmosets (tamarins) after three high dose ($5 \times 10^9$ pfu, $1 \times 10^{10}$ pfu and $2 \times 10^{10}$ pfu), intramuscular immunizations and viral challenge, full protection was obtained.

For certain highly infectious diseases, such as rabies, there is a demand for an effective vaccine. Desirably, a vaccine should be effective at a low dosage to control the occurrence of side effects or to enable sufficient amounts of vaccine to be introduced into animals in the wild. Currently, a vaccinia rabies glycoprotein (VRG) vaccine is being used for oral wildlife immunization [B. Brochier et al, Vaccine, 12:1368–1371 (1994)]. However, doses above $10^6$ pfu are required to induce complete protection.

There thus remains a need in the art for a method of vaccinating a human or animal against rabies, which method is safe and highly effective.

SUMMARY OF THE INVENTION

The inventors have surprisingly found a method of vaccinating a human and/or animal against rabies using an adenovirus defective vaccine composition, which produces a high level of protection upon administration of a low vaccine dose. For example, vaccination with a rabies vaccine composition described herein has been found to require as little as a single dose of $10^4$ pfu of rabies vaccine vector to induce complete protection. This effect is also accomplished by administration routes other than the oral route.

Thus, in one aspect, the invention provides a method of vaccinating a human or animal against rabies comprising administering to said human or animal an effective amount of a replication-defective recombinant adenovirus vaccine containing DNA encoding a rabies which elicits a protective immune response against infection by the rabies virus. This adenovirus of the invention contains at least a partial, but functional, deletion of the Ad E3 gene. Further in the site of the E1a/E1b deletion which renders the Ad replication-defective, the recombinant virus contains a sequence comprising a non-adenovirus promoter directing the replication and expression of the DNA encoding the rabies virus protein. A preferred embodiment of this aspect is the recombinant replication-defective Adrab.gp adenovirus containing DNA encoding a rabies virus G glycoprotein.

Other aspects and advantages of the present invention are described further in the following detailed description of the preferred embodiments thereof.

BRIEF DESCRIPTION OF THE DRAWINGS

FIG. 1A is a schematic representation of the 1650 bp rabies glycoprotein gene from Evelyn Rockitniki Abelseth strain excised from the pSG5.ragp plasmid by cleavage with BglII. The 1650 bp sequence spans nucleotide 1178 to 2827 of SEQ ID NO: 1.

FIG. 1B is a schematic map of the pAd. CMVlacZ (also known as H5.020CMVlacZ) plasmid, which contains adenovirus map units (m.u.) 0–1 as represented by the black bar at the top of the circular plasmid, followed by a cytomegalovirus enhancer/promoter (CMV enh/prom) represented by the striped arrow to the right of the black bar, a human betagalactosidase gene represented by the dark gray bar at the righthand side of the circular plasmid; a polyadenylation signal represented by the short white bar at the bottom of the circular plasmid, adenovirus m.u. 9–16 represented by the long black bar at the lower lefthand portion of the circular plasmid and plasmid sequences from plasmid pAT153 including an origin of replication and ampicillin resistance gene represented by the light gray bar at the upper lefthand portion of the circular plasmid. Restriction endonuclease enzymes are represented by conventional designations in this plasmid. NotI digestion removes the LacZ gene from this plasmid.

FIG. 1C is a schematic map of the plasmid pAdCM-V.rabgp which results from blunt end cloning of the BglII fragment of pSG5.ragp to the larger NotI fragment of pAdCMV.lacZ. pAdCMV.rapgp [SEQ ID NO: 1] contains adenovirus m.u. 0–1 as represented by the black bar at the top of the circular plasmid (nucleotides 12 to 364 of SEQ ID NO: 1); followed by a cytomegalovirus enhancer/promoter (CMV enh/prom) represented by the striped arrow to the right of the black bar [nucleotides 382 to 863 of SEQ ID NO: 1]; a rabies glycoprotein gene represented by the dotted bar at the righthand side of the circular plasmid (nucleotides 1178 to 2827 of SEQ ID NO: 1); a polyadenylation signal represented by the short white bar at the lower righthand portion of the circular plasmid [nucleotides 2836–3034 of SEQ ID NO: 1]; adenovirus m.u. 9–16 represented by the long black bar at the lower portion of the circular plasmid (nucleotides 3061 to 5524 of SEQ ID NO: 1); and plasmid sequences from plasmid pAT153 including an origin of replication and ampicillin resistance gene represented by the light gray bar at the upper lefthand portion of the circular plasmid (nucleotides 5525 to 8236 of SEQ ID NO: 1). Restriction endonuclease enzymes are represented by conventional designations.

FIG. 1D is a schematic map of recombinant adenovirus Adrab.gp (also known as H5.020CMV.rab), which results from homologous recombination between pAdCMV.rabgp and Ad strain dl7001. Ad dl7001 is an Ad5 variant that carries an approximately 3 kb deletion of the Ad5 sequence (GenBank Accession No. M73260) between m.u. 78.4 through 86. The CMV/rabies glycoprotein/pA minicassette of pAd. CMVrab is inserted between deleted adenovirus m.u.1 and 9, with the remaining Ad5 m.u. 9–100 having the above-mentioned E3 gene deletion. Restriction endonuclease enzymes are represented by conventional designations.

FIG. 2 provides the nucleotide sequence of pAdCMV.rab plasmid [SEQ ID NO: 1] and the amino acid sequence encoded thereby [SEQ ID NO: 2], which is substantially similar to the pAd. CMVlacZ plasmid, but which contains the rabies glycoprotein sequence in place of the lacZ gene.

DETAILED DESCRIPTION OF THE INVENTION

Figure 3:
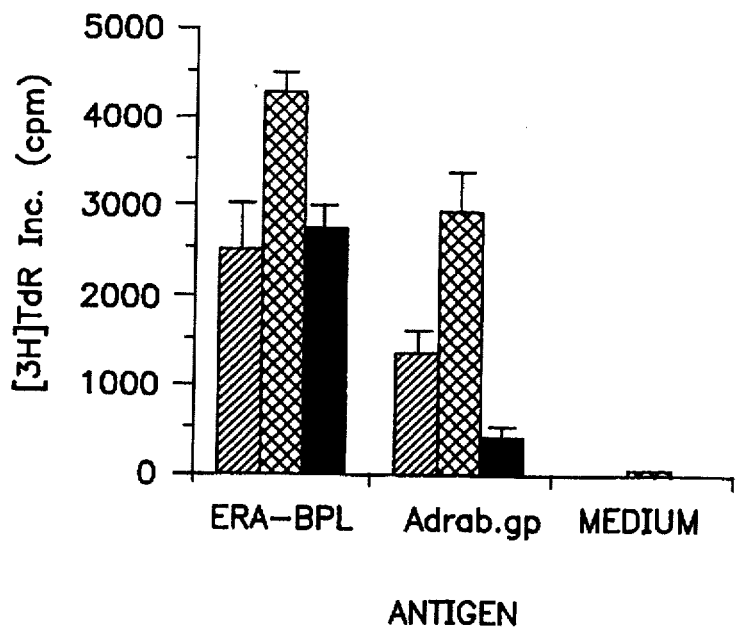
FIG. 3 is a bar graph plotting $^3$H-thymidine ([3H]TdR) incorporation, measured at counts per minute ±standard deviation (cpm±SD), for irradiated splenocytes plated at $5 \times 10^5$ cells per well of a round bottom microtiter plate and incubated with 5 (diagonally striped), 1 (cross-hatched) or 0.2 (solid) µg/ml of betapropionolactone-inactivated Evelyn Rockitniki Abelseth rabies strain (ERA-BPL) or approximately 1 (diagonally striped), 0.1 (cross-hatched), and 0.01 (solid) pfu of Adrab.gp per cell or medium only as a negative control for 60 minutes at 37° C. As described in Example 2B, after cloned T cells were added, cells were pulsed two days later for 6 hours with $^3$H-thymidine, harvested and counted in a β-counter.

The present invention provides a method of effectively inducing a protective immune response to infection by rabies virus by use of a vaccine composition including a recombinant replication-defective adenovirus, previously used for gene therapy. As discussed herein, the inventors have surprisingly found that use of such a recombinant Ad, described in detail below, provides substantially complete immune protection in vaccinates.

By "substantially complete" protection is meant when administered in an effective amount, the recombinant adenovirus presents a rabies virus immunogenic protein in such a manner that a protective immune response is observed in substantially all vaccinates after a single administration. By "substantially all" is meant greater than 90% of the vaccinates. Unexpectedly, the recombinant vaccine permits successful vaccination with very few booster administrations. Also unexpectedly, the recombinant vaccine permits vaccination at an unexpectedly lower dosage than is normally used in similar vaccines in which the same protein is present in another recombinant virus. For example, immunization of mice with a single dose of as little as $10^4$ pfu of the recombinant, replication defective Ad containing rabies glycoprotein has been observed to induce complete protection against rabies infection.

While not wishing to be bound by theory, the inventors currently believe that this recombinant, replication defective Ad vaccine is advantageous over, e.g., the vaccinia vaccine, because it permits lower doses of rabies antigen to be expressed for an extended period of time by a non-lytic virus. In contrast, although vaccinia expresses higher doses of a rabies virus antigen, it is a lytic virus which causes a rapid demise of infected cells. The finding that the recombinant replication-defective Adrab.gp virus used in the method of the present invention is more efficacious than the currently used vaccinia rabies (VRG) vaccine is unexpected and incompatible with current thinking that the antigenic dose governs the magnitude of the immune response. The use of the recombinant replication defective adenovirus also confers safety and efficacy advantages over other vaccine carriers, such as vaccinia.

With respect to safety, the present invention provides a recombinant replication-defective Ad which is thus highly unlikely to spread within a host or among individuals, particularly in view of the fact that the recombinant, E1-deleted dl7001 Ad virus, which is the backbone of the exemplary replication defective recombinant Ad used in the examples below has already been approved for use in humans for gene therapy, i.e., for the replacement of faulty or missing genes. The recombinant virus lacks oncogenic potential because the E1 gene that can function as an oncogene in some adenovirus strains has been deleted. Further, cells infected with the recombinant, replication defective adenovirus are completely eliminated by CD8 T cells within 21 days in immunocompetent hosts.

With respect to efficacy, the recombinant, replication defective Ad containing a sequence encoding the rabies virus glycoprotein of this invention is highly efficacious at inducing cytolytic T cells and antibodies to the inserted rabies virus glycoprotein expressed by the recombinant virus. This has been demonstrated with a recombinant, replication defective Ad of the invention where the recombinant Ad has been administered to animals by other than the oral route.

The recombinant virus of this invention is also surprisingly more effective as a rabies vaccine than other, previously reported, replication defective adenovirus vaccines containing antigens from other viruses. See, for example, Ragot et al, Eliot et al, and Jacobs et al, all cited above. In contrast to the other replication defective adenovirus vaccines, the rabies vaccine composition useful in the present invention can be used at lower doses. This vaccine can also be administered in a single inoculation to obtain substantially complete protection.

For these reasons, the recombinant replication-defective adenovirus of the invention and particularly the preferred embodiment which makes use of the pAdCMV.lacZ (or H5.020CMVlacZ) Ad vector described below, can be used as a prophylactic or therapeutic vaccine against rabies virus.

I. The Recombinant Adenovirus

As used herein, the term "minicassette" refers to the nucleotide sequence comprised of (a) a non-Ad promoter, which directs the replication and expression of (b) the following nucleotide sequence which encodes a rabies virus protein immunogen, which is followed by (c) a polyA nucleotide sequence. By "vector or plasmid" is meant the construct comprised of 5' sequences of the Ad virus (usually Ad m.u. 0–1) deleted of the E1 gene (which occurs between Ad m.u. 1–9), which may contain a rabies virus glycoprotein nucleotide sequence, but which does not contain the 3' end of the Ad virus (generally between about Ad m.u. 16 to 100), but rather conventional plasmid sequences. This vector does not contain all of the genes essential to a replicative Ad virus. By "recombinant, replication defective Ad" is meant the infectious recombinant virus, deleted of its E1 gene, into which location is inserted the minicassette, and which contains all of the 3' sequences essential to an infectious virus except for a functional deletion in the E3 gene region.

The recombinant virus of the method of the invention is a replication-defective recombinant adenovirus containing a deletion of its E1 gene and at least a partial, functional deletion of its E3 gene. In the site of the E1 deletion a minicassette is inserted, which comprises a nucleotide sequence encoding a rabies virus protein immunogen and a non-adenovirus promoter directing the replication and expression of the nucleotide sequence encoding the rabies virus protein.

Any Ad that infects the target cells is appropriate for use in this invention. Desirable adenoviruses are human type C adenoviruses, including serotypes Ad2 and Ad5. The DNA sequences of a number of adenovirus types, including type Ad5, are available from GenBank [Accession No. M73260]. The adenovirus sequences may be obtained from any known adenovirus type, including the presently identified 41 human types [Horwitz et al, Virology, 2d ed., B. N. Fields, Raven Press, Ltd., New York (1990)]. Similarly, adenoviruses known to infect other animals may also be employed in this invention. The selection of the adenovirus type and strain is not anticipated to limit the following invention. A variety of adenovirus strains are available from the American Type Culture Collection, Rockville, Md, or available by request from a variety of commercial and institutional sources. In the following exemplary embodiment, an adenovirus type 5 (Ad5) sequence obtained from GenBank [Acc. No. M73260] is used for convenience.

Adenoviruses of the present invention are replication defective, i.e., intact adenoviruses which have been rendered replication defective by deleting the early gene locus that encodes E1a and E1b. See, K. F. Kozarsky and J. M. Wilson, *Curr. Opin. Genet. Dev.*, 3:499–503 (1993). Similarly, a replication defective adenovirus may be designed by deleting less than the entire E1a and E1b locus, but enough to functionally disable the E1 genes.

An additional characteristic of the Ad useful in this invention is that the E3 gene is deleted, i.e., from about m.u. 78.5 to about m.u. 84.3 of Ad5. While the presently preferred embodiment contains a complete deletion of that sequence, it may be possible to partially delete the E3 sequence to disable the functional abilities of the E3 gene.

A preferred recombinant Ad virus may be produced by using a plasmid vector pAd.CMVlacZ as described in FIG. 1B. This plasmid contains adenovirus sequences Ad m.u. 0–1 (i.e., it is fully deleted of E1a and E1b genes), after which a selected minigene may be inserted, e.g., the rabies glycoprotein under control of a heterologous promoter and other regulatory sequences, if desired, followed by the sequence Ad m.u.9 to 16 and plasmid sequences. When this vector is manipulated to place a minicassette into the E1 deletion site, and supplied with the remaining 3' Ad sequences with a full deletion of E3 and cultured in a helper cell line, the resulting recombinant adenovirus functions as a vaccine. This recombinant virus, called Adrab.gp or H5020.CMVrab, is described in detail in Example 1 and in flow chart form in FIGS. 1A through 1D.

The preferred recombinant Ad of this invention contains a minicassette which uses the cytomegalovirus (CMV) promoter [see, e.g., Boshart et al, *Cell*, 41:521–530 (1985)] to control the expression of the inserted heterologous gene. The promoter is inserted in the site of the E1 deletion and directs the replication and expression of the gene encoding the rabies virus protein. However, this invention is not limited by the selection of the promoter, except that the promoter should be heterologous to the Ad virus, i.e., the E1 Ad promoter is replaced using techniques known to those of skill in the art. Other desirable promoters include the Rous sarcoma virus LTR promoter/enhancer, the SV40 promoter, and the chicken cytoplasmic B-actin promoter [T. A. Kost et al, *Nucl. Acids Res.*, 11(23):8287 (1983)]. Still other promoter/enhancer sequences may be readily selected by one of skill in the art.

As discussed above, in the site of the E1 deletion, and under control of a promoter heterologous to Ad, a nucleic acid sequence, preferably in the form of DNA, encodes a rabies virus protein and is inserted using techniques known to those of skill in the art. The rabies virus nucleic acid sequence encodes a protein which is desirably capable of inducing an immune response to rabies virus. In a particularly preferred embodiment, the protein is the rabies G glycoprotein [see, U.S. Pat. No. 4,393,201]. A variety of rabies strains are well known and available from academic and commercial sources, including depositaries such as the American Type Culture Collection, or may be isolated using known techniques. The strain used in the examples below is the Evelyn Rockitniki Abelseth (ERA) strain. However, this invention is not limited by the selection of the rabies strain.

In a preferred embodiment, cDNA encoding the rabies virus glycoprotein is inserted under control of a CMV promoter into the pAdCMV.lacZ (or H5.020CMVlacZ) Ad vector and supplied with the essential genes for infectivity and viral formation in a helper cell line using standard techniques, as described in detail in Example 1. Immunization studies revealed that a single administration of the resulting recombinant replciation defective virus conferred complete protection at a relatively low dose following challenge with rabies virus.

II. Formulation of Vaccine

A recombinant replication defective Ad bearing a gene encoding a rabies virus immunogenic protein may be administered to a human or veterinary patient, preferably suspended in a biologically compatible solution or pharmaceutically acceptable delivery vehicle. A suitable vehicle is sterile saline. Other aqueous and non-aqueous isotonic sterile injection solutions and aqueous and non-aqueous sterile suspensions known to be pharmaceutically acceptable carriers and well known to those of skill in the art may be employed for this purpose.

Optionally, a vaccinal composition of the invention may be formulated to contain other components, including, e.g. adjuvants, stabilizers, pH adjusters, preservatives and the like. Such components are well known to those of skill in the vaccine art.

III. Administration of Vaccine

The recombinant, replication defective viruses are administered in an "effective amount", that is, an amount of recombinant virus that is effective in a route of administration to transfect the desired cells and provide sufficient levels of expression of the selected gene to provide a vaccinal benefit, i.e., protective immunity.

Conventional and pharmaceutically acceptable routes of administration include intranasal, intramuscular, intratracheal, subcutaneous, intradermal, rectal, oral and other parental routes of administration. Routes of administration may be combined, if desired, or adjusted depending upon the immunogen or the disease. For example, in prophylaxis of rabies, the subcutaneous, intratracheal and intranasal routes are preferred. The route of administration primarily will depend on the nature of the disease being treated.

Doses or effective amounts of the recombinant replication defective Ad virus will depend primarily on factors such as the selected rabies virus gene, the age, weight and health of the animal, and may thus vary among animals. For example, a prophylactically effective amount or dose of the Ad vaccine is generally in the range of from about 100 µl to about 10 ml of saline solution containing concentrations of from about $1 \times 10^4$ to $1 \times 10^7$ plaque forming units (pfu) virus/ml. A preferred dose is from about 1 to about 10 ml saline solution at the above concentrations. The levels of immunity of the selected gene can be monitored to determine the need, if any, for boosters.

Currently, when vaccinating against rabies, the preferred dose is about $10^4$ pfu of the recombinant virus per mouse, preferably suspended in about 0.1 mL saline. Thus, when vaccinating against rabies infection, a larger animal would preferably be administered about a 1 mL dose containing about $1 \times 10^5$ Adrab.gp pfu suspended in saline. Following an assessment of antibody titers in the serum, optional booster immunizations may be desired.

The following examples illustrate the preferred methods for preparing the vectors and the recombinant viruses used in the vaccine and method of the invention. These examples are illustrative only and do not limit the scope of the invention.

EXAMPLE 1

Production and Purification of Vectors and Viruses

A. Adrab.gp

A recombinant, replication defective adenovirus expressing the rabies virus G protein of the Evelyn Rockitniki Abelseth (ERA) strain of rabies virus [ATCC VR-332; U.S. Pat. No. 3,423,505] (ERA) was constructed as follows. See the flowchart of FIGS. 1A to 1D.

The 1650 bp rabies virus G cDNA (nucleotides 1178 to 2827 of SEQ ID NO: 1) was purified from the pSG5rab.gp plasmid [S. R. Burger et al, *J. Gen. Virol.*, 72:359–367 (1991)] upon digestion with BglII, and blunt-ended with Klenow to supply the G gene. See also U.S. Pat. No. 4,393,201, issued Jul. 12, 1983.

The pAd. CMVlacZ vector [J. Wilson et al, *Hum. Gene Ther.*, 5:501–519 (1994); K. Kozarsky et al, *J. Biol. Chem.*, 269:13695–13702 (1994)], which contains Ad5 m.u. 0–1, followed by the cytomegalovirus (CMV) enhancer/promoter, the beta galactosidase (lacZ) gene, a polyadenylation signal (pA), adenovirus m.u. 9–16 and plasmid sequences from plasmid pAT153 including an origin of replication and ampicillin resistance gene, was completely digested with NotI to remove the lacZ gene and provide an ~5.6 kb backbone.

The cDNA encoding the rabies G protein, described above, was inserted into this 5.6 kb fragment via blunt-end cloning to generate pAdCMV.rabgp, which is similar to pAd. CMVlacZ but contains the rabies sequence in place of the lacZ gene. The appropriate orientation of the insert was confirmed by restriction enzyme mapping. pAdCMV.rabgp [SEQ ID NO: 1] contains adenovirus m.u. 0–1 (nucleotides 12 to 364 of SEQ ID NO: 1); followed by a cytomegalovirus enhancer/promoter (nucleotides 382 to 863 of SEQ ID NO: 1); the rabies glycoprotein gene (nucleotides 1178 to 2827 of SEQ ID NO: 1); a polyadenylation signal (nucleotides 2836–3034 of SEQ ID NO: 1); adenovirus m.u. 9–16 (nucleotides 3061 to 5524 of SEQ ID NO: 1); and plasmid sequences from plasmid pAT153 (nucleotides 5525 to 8236 of SEQ ID NO: 1). The remaining nucleotides of SEQ ID NO: 1 are the result of cloning and plasmid construction.

To provide a recombinant virus capable of infecting a cell, the 3' end of the adenovirus sequence was needed to replace the pAT153 plasmid sequences of pAdCMV.rabgp. The plasmid pAdCMV.rabgp was linearized with NheI. The linearized plasmid was co-transfected into 293 packaging cells [ATCC CRL 1573] which contain and express the transforming genes of human adenovirus type 5 to allow replication of the adenovirus [F. L. Graham et al, *J. Gen. Virol.*, 36:59–72 (1977)]. The transfected packaging cells were grown in DMEM with 10% FBS without HEPES buffer in a 5% $CO_2$ incubator with an E3 deleted Ad5 DNA [Ad5dl7001, a variant that carries a 3 kb deletion between m.u. 78.4 through 86 in the nonessential E3 region (provided by Dr. William Wold, Washington, University, St. Louis, Mo.)]. This Ad5dl7001 had been digested with a restriction enzyme ClaI to remove the left end, i.e., 917 bp from the 5' end of the adenovirus sequence, rendering the DNA non-infectious.

Following the co-transfection, only products of homologous recombination which occurred between Ad m.u. 9–16 of the pAdCMV.rabgp and the 5' deleted-Ad5dl7001 could produce replicative Ad virus in 293 cells. That is, when homologous recombination occurred, the 3' end of pAd.rabgp from about Ad m.u. 9 to about m.u. 16 and all of the plasmid sequence was swapped with the 3' end of the 5' truncated Ad5dl7001 virus, from about Ad m.u. 9 through m.u. 100.

Several recombinant viral plaques were harvested and tested for expression of the rabies virus G protein as described below. One recombinant, replication defective clone termed Adrab.gp was purified by two rounds of plaque purification and used for further studies and is illustrated schematically in FIG. 1D above.

The recombinant, replication defective Ad Adrab.gp contains Ad5 m.u. 0–1, followed by the CMV enhancer/promoter, the rabies G gene, a pA site, and Ad5 m.u. 9–78.4 and 86–100. Adrab.gp was deposited with the American Type Culture Collection, 12301 Parklawn Drive, Rockville, Md., 20852 under Accession No. VR-2554 on Feb. 25, 1997 under the deposit requirements of the United States Patent and Trademark Office.

B. H5.010CMVlacZ

The recombinant replciation defective Ad, H5.010CMVlacZ, is substantially identical to Adrab.gp, except that this virus contains *E. coli* lacZ in place of the rabies G protein and only a partial deletion of E3.

The plasmid pAd. CMVlacZ described above, was linearized with NheI and co-transfected into 293 cells with a partially E3 deleted Ad5 DNA (sub 360 DNA, H5sub360), which had been digested with ClaI to eliminate the sequence of m.u. 83.5 to 85. As above, homologous recombination, followed by plaqing and harvesting produced the resulting recombinant adenovirus, designated H5.010CMVlacZ. This virus contains the sequence from Ad5 m.u. 0–1, followed by the CMV enhancer/promoter, the *Escherichia coli* lacZ gene, a pA site, and Ad5 m.u. 9–83.5 and 85–100.

C. Viral Propagation and Purification

The adenoviral recombinants, Adrab.gp H5.010CMVlacZ, and Ad5dl7001, a replication competent adenovirus, on 293 cells for 72 hours. Virus was recovered on the third round of freeze-thawing. Cell-free supernatants were either used directly or they were further purified by CsCl density centrifugation. Viral stocks were titrated on 293 cells using a plaque assay.

EXAMPLE 2

Immunofluorescence and T Cell Studies

To confirm that the Adrab.gp recombinant virus expresses the rabies virus G protein on infected cells in a form recognized by antibodies and cytolytic T cells directed against rabies virus, a series of in vitro experiments were performed initially.

A. Indirect Immunofluorescence

To assess the conformation of the G protein as expressed by the Adrab.gp virus, HeLa cells [which had been maintained in Dulbecco's minimal essential medium (DMEM) supplemented with 10% FBS, HEPES buffer and antibiotics in a 10% $CO_2$ incubator] were infected for 48 hours with 1 pfu of Adrab.gp virus per cell or as a control with H5.020CMVlacZ. Cells were stained 24 hours later by an indirect immunofluorescence assay using three MAbs (designated 523-11, 509-6, and 1112-1, and prepared using a 1:100 to 1:1000 dilution of ascitic fluid) to different conformation-dependent binding sites of the rabies virus G protein. The B cell hybridoma cells 509-6, 1112-1, and 523-11 secrete antibodies to different antigenic sites of the rabies virus G protein (509-6 to site I, 1112-1 to site II, and 523-11 to site III [T. J. Wiktor et al, *Proc. Natl. Acad. Sci. USA*, 75:3938–3945 (1978)]. These hybridoma cells were grown in DMEM supplemented with 10% FBS. Ascetic fluid was prepared in BALB/c mice. The assay was performed as follows.

The HeLa cells were infected for various times with 1 pfu of recombinant adenovirus or with 1 pfu of the vaccinia VRG virus described above per cell in 24-well Costar plates seeded with $5\times10^5$ cells per well. Cells were harvested at varied times after infection by treatment with trypsin and incubated for 60 minutes on ice with the MAbs identified above. Cells were washed once with phosphate-buffered saline (PBS) and then incubated with a FITC-labeled goat anti-mouse immunoglobulin (Ig) antibody. Cells were washed and analyzed by a fluorescence activated cell sorter (FACS). Alternatively cells adherent to glass cover slips were stained with the same antibody preparations for subsequent analysis with confocal microscopy.

For all of the antibodies, Adrab.gp virus-infected cells exhibited surface staining with the antibody, while cells infected with the control recombinant virus expressing lacZ were negative.

B. T Cell Proliferation Assay

Further in vitro studies showed that the recombinant virus Adrab.gp induced proliferation of a rabies virus G protein specific T helper cell clone in the presence of syngeneic, γ-irradiated splenocytes (FIG. 3).

A rabies virus-specific helper T cell clone, obtained from splenocytes of VRG immune C3H/He mice in the inventors' laboratory, was cultured ($2 \times 10^4$ cells/well) in 96-well round-bottom microtiter plate with $5 \times 10^5$ irradiated syngeneic C3H/He splenocytes pretreated with different antigen preparations (1, 0.1 and 0.01 pfu Adrab.gp per cell) in DMEM supplemented with 2% FBS and $10^{-6}$M 2-mercaptoethanol and 10% rat Concanavalin A supernatant as a lymphokine source as described previously [L. Otvos, Jr., Biochim. Biophys. Acta, 1224:68–76 (1994)]. Proliferation of the cloned T cells was assessed 48 hours later by a 6 hour pulse with 0.5 µCi of $^3$H-thymidine as described in H. C. J. Ertl et al, Eur. J. Immunol., 21:1–10 (1991). Furthermore, mouse fibroblasts infected with the Adrab.gp recombinant virus were rendered susceptible to lysis by rabies virus G protein induced H-2 compatible cytolytic T cells.

Together these in vitro experiments demonstrated that Adrab.gp causes expression of the rabies virus G protein in a form that is readily recognized by both rabies virus-specific antibodies and T cells of the helper and the cytolytic subset. Specificly, FIG. 3 illustrates that Adrab.gp induces proliferation of a rabies virus G protein T helper cell clone in the presence of antigen presenting cells.

EXAMPLE 3

Immunization Studies

In the next set of experiments, mice were immunized with the Adrab.gp recombinant virus at several doses using different routes of immunization as follows. Groups of eight to twelve week old outbred ICR [Harlan Sprague-Dawley (Indianapolis, IN)] or C3H/He mice [The Jackson Laboratories (Bar Harbor, Me.)] were injected subcutaneously (s.c.), orally (per os), intranasally (i.n.), or upon anesthesia and surgical exposure of the trachea intratracheally (i.t.), with the recombinant adenoviruses of the previous examples diluted in 100 to 150 µl of saline. VRG [which had been propagated on HeLa cells as described in T. J. Wiktor et al, Proc. Natl. Acad. Sci. USA, 81:7194–7198 (1984)] was given s.c. Mice were bled by retro-orbital puncture in regular intervals after immunization to assess serum antibody titers.

The challenge virus standard (CVS)-24 strain of rabies virus, that is antigenically closely related to the ERA strain but shows higher virulence in mice, was derived from brain suspensions of infected newborn ICR mice [T. J. Wiktor et al, J. Virol., 21:626–633 (1977]. Mice were challenged with 10 mean lethal doses (LD$_{50}$) of CVS-24 virus given intra- muscularly (i.m.) into the masseter muscle; they were observed for the following 3 weeks for symptoms indicative of a rabies virus infection. Mice that developed complete bilateral hind leg paralysis (proceeding death by 24 to 48 hours) were euthanized for humanitarian reasons.

A. Virus Neutralizing Antibodies

Groups of ICR mice were immunized in three separate experiments with the different recombinant viruses given at the doses in Table 1 below either i.m., i.n., i.t., or per os. Mice inoculated into the trachea or i.n. were anesthetized prior to vaccination. Mice were bled 10 to 14 days later after a single immunization and serum antibody titers to rabies virus were tested by a neutralization assay. Virus neutralizing antibody (VNA) titers were determined on BHK-21 cells using infectious ERA virus at 1 pfu per cell [B.D. Dietzschold et al, Virology, 161:29–36 (1987)].

Table 1 below illustrates the data expressed as neutralization titers which are the reciprocal of the serum dilution resulting in a 50% reduction in the number of infected cells. Samples were assayed in duplicate in serial 3-fold dilutions starting with a dilution of 1:5. Standard deviations were within 10% for any given experiment.

As illustrated by the results in Table 1, virus given s.c., i.t., or i.n. induced a potent neutralizing antibody response if given at $10^6$ pfu. Oral immunization with Adrab.gp or systemic immunization with H5.020CMVlacZ failed to induce a measurable antibody response to rabies virus. The antibody responses to different doses of the recombinant replication-defective Adrab.gp were clearly superior to the response induced by the VRG recombinant. For example, the antibody titers of mice inoculated with as little at $10^4$ pfu of Adrab.gp were more than 10 times higher than those of mice infected with $10^6$ pfu of VRG (Table 1).

TABLE 1

Adrab.gp Recombinant Induces Neutralizing Antibodies to Rabies Virus

| Vaccine | Dose | Route of Immunizat'n | Time After | VNA titer Immunizat'n |
|---|---|---|---|---|
| Adrab.gp | $2 \times 10^6$ | s.c. | day 10 | 3,645 |
| Adrab.gp | $2 \times 10^5$ | s.c. | day 10 | 405 |
| Adrab.gp | $2 \times 10^4$ | s.c. | day 10 | 405 |
| VRG | $2 \times 10^6$ | s.c. | day 10 | 45 |
| VRG | $2 \times 10^5$ | s.c. | day 10 | 15 |
| VRG | $2 \times 10^4$ | s.c. | day 10 | 5 |
| None | — | — | day 10 | <5 |
| Adrab.gp | $10^4$ | s.c. | day 14 | 1,215 |
| Adrab.gp | $10^3$ | s.c. | day 14 | 405 |
| Adrab.gp | $10^2$ | s.c. | day 14 | <5 |
| Adrab.gp | $10^6$ | i.n. | day 14 | 1,215 |
| Adrab.gp | $10^6$ | i.t. | day 14 | 3,645 |
| Adrab.gp | $10^6$ | per os | day 14 | <5 |
| None | — | — | — | <5 |

B. Cell-mediated Cytolysis

In addition to neutralizing antibodies, mice inoculated s.c. with Adrab.gp virus developed rabies virus G protein-specific cytolytic T cells able to kill H-2 compatible L929 target cells stably transfected with a plasmid vector expressing the rabies virus G protein under the control of the SV40 early promoter [Z. Q. Xiang et al, J. Virol. Meth., 47:103–116 (1994)].

L929 mouse fibroblasts were maintained in Dulbecco's minimal essential medium (DMEM) supplemented with 10% fetal bovine serum (FBS), HEPES buffer and antibiotics in a 10% CO$_2$ incubator. L929 cells stably transfected with pSG5rab.gp [S. R. Burger et al, cited above], expressing the rabies virus G protein as well as L929 cells transfected with pSV2neo [ATCC Accession No. 37149] were maintained in 10% DMEM supplemented with 10% FBS. These cell lines used as target cells for cell-mediated cytolysis assays have been described in detail previously [Z.Q. Xiang et al, *J. Virol. Meth.*, 47:103–116 (1994)].

Briefly, splenocytes were harvested from immunized C3H/He mice. Single cells were prepared and incubated at $6 \times 10^6$ cells per well with 1 pfu per cell of the Adrab.gp recombinant virus in 1.6 ml of DMEM supplemented with $10^{-6}$M 2-mercaptoethanol and 2% FBS for 5 days in a humidified 10% $CO_2$ incubator. The effector cells were then co-cultured with $^{51}$Cr-labeled L929 cells expressing the rabies virus G protein upon stable transfection with the pSG5rab.gp vector at varied effector-to-target cells ratios. To assess spontaneous release, $^{51}$Cr-labeled target cells were incubated with medium; to determine maximal release target cells were co-cultured with 10% sodium dodecyl sulfate. Cell-free supernatants were harvested 4 hours later and radioactivity was measured. Percentage of specific lysis was calculated by using the formula [Y. Yang et al, *Immunity*, 1:433–442 (1994)]:

100 × [(Release in presence of effectors − spontaneous release)/(Maximal release − spontaneous release)]

Figure 4A:
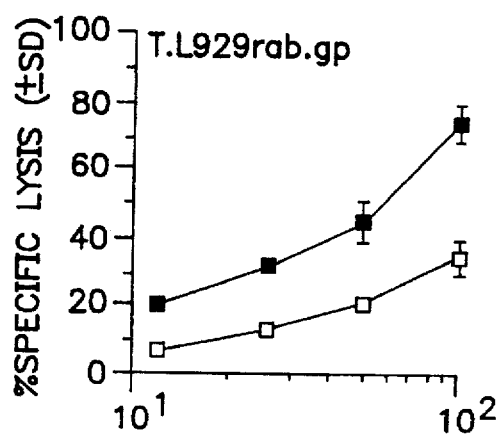
FIG. 4A is a graph plotting % specific lysis (means of triplicates±SD) vs. effector:target cell ratio for groups of C3H/He mice inoculated with $2 \times 10^6$ pfu of Adrab.gp (solid box) or H5.020CMVlacZ (open box), as described in Example 4B. Splenocytes were harvested 14 days later and co-cultured for 5 days with 1 pfu of Adrab.gp virus per cells. Activated lymphocytes were then tested at different E:T ratios on H-2 compatible L929 cells stably transfected with a rabies virus G protein-expressing vector (t. L929rab.gp) in a 4 hour $^{51}$Cr-release assay.
Figure 4B:
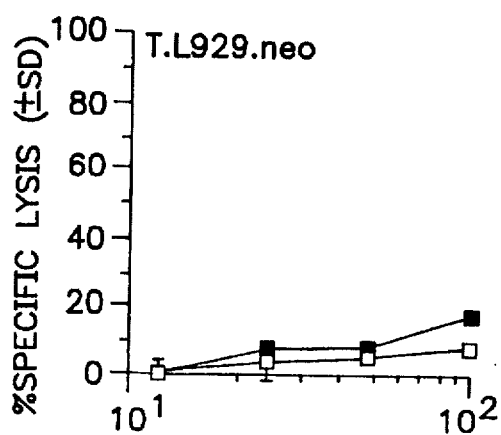
FIG. 4B is a graph of an experiment similar to FIG. 4A, but in which the activated lymphocytes were tested at different E:T ratios on H-2 compatible L929 cells stably transfected with a neomycin-expressing vector (t.L929.neo) in the $^{51}$Cr-release assay, as a control.
Figure 5A:
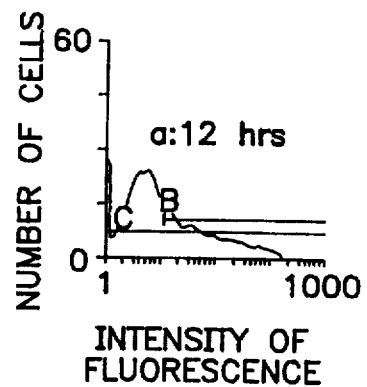
FIG. 5A is a graph plotting number of cells vs. intensity of fluorescence for L929 fibroblasts plated in 24-well Costar plates in medium supplemented with 2% fetal bovine serum (FBS) following infection with 1 pfu/cell of VRG, as described in Example 5 below. Cells harvested 12 hours after infection and stained by indirect immunofluorescence with monoclonal antibody (MAb) 509-6 were analyzed by fluorescence activated cell sorting (FACS). The line on the graph labeled "B" is the threshold below which 99% of the population are negative. Line "C" represents the region that encompasses all events on the histogram.
Figure 5B:
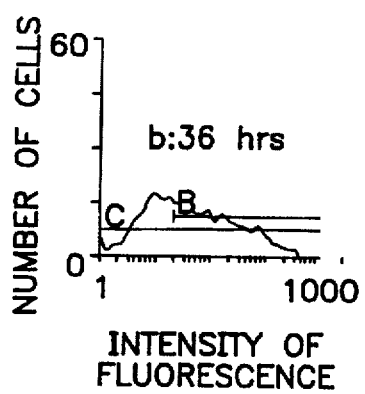
FIG. 5B is a graph similar to FIG. 5A above, except the cells were harvested 36 hours after infection.
Figure 5C:
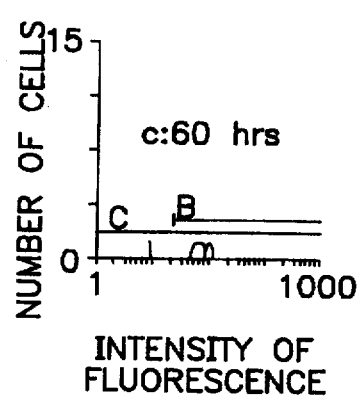
FIG. 5C is a graph similar to FIG. 5A above, except the cells were harvested 60 hours after infection.
Figure 5D:
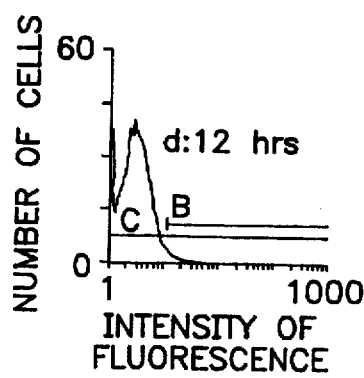
FIG. 5D is a graph similar to FIG. 5A above, except the cells, harvested 12 hours after infection, were stained using cells treated only with the fluorescein isothiocyanate (FITC) -labeled goat anti-mouse immunoglobulin (Ig) as a control.
Figure 5E:
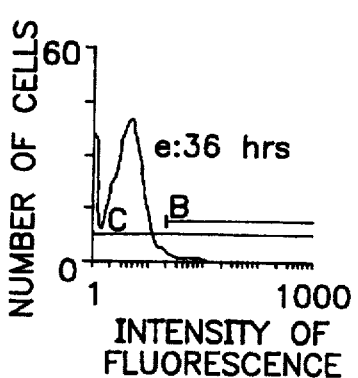
FIG. 5E is a graph similar to FIG. 5D above, except the cells were harvested 36 hours after infection.
Figure 5F:
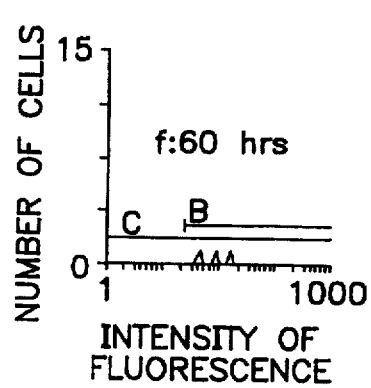
FIG. 5F is a graph similar to FIG. 5D above, except the cells were harvested 60 hours after infection.
Figure 5G:
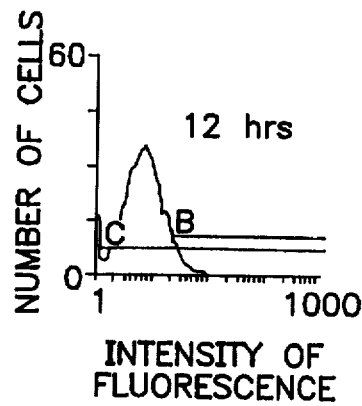
FIG. 5G is a graph similar to FIG. 5A above, except the cells were infected with 1 pfu Adrab.gp virus, and cells were harvested 12 hours after infection.
Figure 5H:
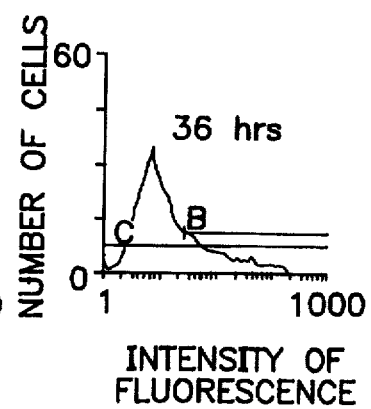
FIG. 5H is a graph similar to FIG. 5G, except the cells were harvested 36 hours after infection.
Figure 5I:
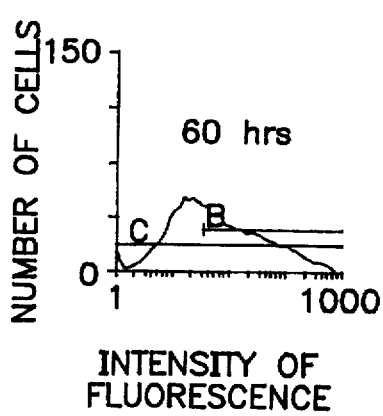
FIG. 5I is a graph similar to FIG. 5G, except the cells were harvested 60 hours after infection.
Figure 5J:
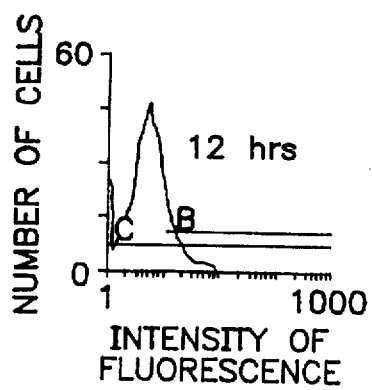
FIG. 5J is a graph similar to FIG. 5G above, except the cells were stained by indirect immunofluorescence using cells treated only with FITC-labeled goat anti-mouse Ig as a control.
Figure 5K:
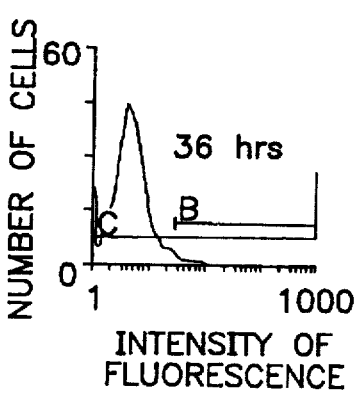
FIG. 5K is a graph similar to FIG. 5J above, except the cells were harvested 36 hours after infection.
Figure 5L:
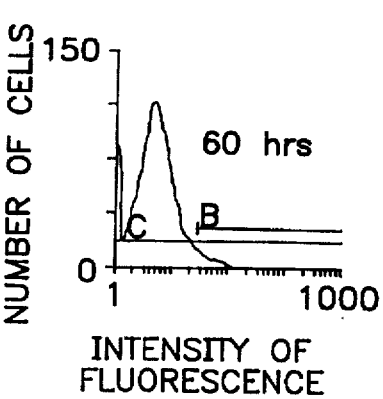
FIG. 5L is a graph similar to FIG. 5J above, except the cells were harvested 60 hours after infection.

The results are illustrated graphically in FIG. 4A, which illustrates that the Adrab.gp construct induces cytolytic T cells to the rabies virus G protein. See, also the results of FIG. 4B, in which lymphocytes were tested at different E:T ratios on an L929 cell line transfected with Adrab.gp or a neomycin expressing control.

EXAMPLE 4

Challenge Studies

Four different experiments were conducted in which mice, immunized as described in Example 3A above, were challenged with 10 $LD_{50}$ of rabies virus. Briefly, mice immunized with the Adrab.gp or the VRG recombinant virus were challenged 2 to 5 weeks after immunization with 10 $LD_{50}$ of the virulent CVS-24 strain of rabies virus given i.m. into the masseter muscle. Mice that subsequently developed complete bilateral hind leg paralysis indicative of a terminal rabies virus infection were euthanized for humanitarian reasons. Survivors were observed for a total of 21 days.

The results are illustrated in Table 2 below. Mice immunized with Adrab.gp i.m., i.t., or i.n. using doses ranging from $10^4$ to $10^6$ pfu were fully protected against infection; 87% of mice inoculated with $10^3$ pfu were protected. All mice immunized with only $10^2$ pfu of the recombinant adenovirus or inoculated with the H5.020CMVlacZ control virus ($2 \times 10^6$ pfu) or with Adrab.gp per as developed a fatal rabies virus encephalitis within 10 days after infection. Mice vaccinated with VRG showed partial protection; the group receiving the highest dose, i.e., $10^6$ pfu, had a mortality rate above 50% raising to ~90% in mice inoculated with $10^4$ pfu of VRG.

TABLE 2

Adrab.gp Recombinant Virus Induces Protective Immunity to Challenge with Rabies Virus

| Vaccine | Dose | Route of immunization | % mortality |
|---|---|---|---|
| Adrab.gp | $2 \times 10^6$ | s.c. | 0 |
| H5.010CMVlacZ | $2 \times 10^6$ | s.c. | 90 |
| Adrab.gp | $2 \times 10^6$ | s.c. | 0 |
| Adrab.gp | $2 \times 10^5$ | s.c. | 0 |
| Adrab.gp | $2 \times 10^4$ | s.c. | 0 |
| VRG | $2 \times 10^6$ | s.c. | 56 |
| VRG | $2 \times 10^5$ | s.c. | 71 |
| VRG | $2 \times 10^4$ | s.c. | 86 |
| None | — | — | 100 |
| Adrab.gp | $10^4$ | s.c. | 0 |
| Adrab.gp | $10^3$ | s.c. | 13 |
| Adrab.gp | $10^2$ | s.c. | 100 |
| None | — | — | 100 |
| Adrab.gp | $10^6$ | i.n. | 0 |
| Adrab.gp | $10^6$ | i.t. | 0 |
| Adrab.gp | $10^6$ | per os | 100 |
| None | — | — | 100 |

EXAMPLE 5

Comparison Studies

The relationship between the magnitude of an immune response and the amount of antigen available to induce naive T and B cells was studied. As determined by immunofluorescence and subsequent analysis by FACS (FIGS. 5A–5L), both the VRG and the Adrab.gp recombinants express comparable levels of the rabies virus G protein but the kinetics of expression are different. Cells infected with the VRG virus express high levels of G protein within 12 hours after infection; these levels increased over the next day. By 60 hours the VRG virus has completely lysed a cell population infected with ~1 pfu of virus per cell.

The same cell line infected with 1 pfu of Adrab.gp per cell shows low expression of the rabies virus G protein on day 1. The level of expression increases until days 3 to 4 after infection and then reaches plateau levels (data shown for days 1 to 3 in FIG. 5A through FIG. 5L). The replication-defective recombinant adenoviruses are non-lytic and maintain stable infection and expression of virus-encoded proteins for extended periods of time. In tissue culture, expression has been shown for 7 days in vivo; using the H5.010CMVlacZ recombinant virus, stable levels of expression were demonstrated in immunocompromised mice for 10 months.

A non-lytic virus, e.g., the recombinant replication defective adenovirus, that expresses antigens for prolonged periods of time might thus be more immunogenic compared to a replicating agent that causes death of the infected cells within 24 to 48 hours, e.g., vaccinia.

Figure 6A:
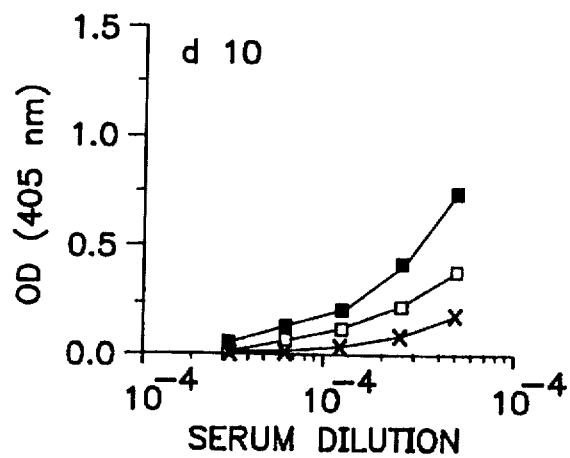
FIG. 6A is a graph plotting optical density at 405 nm vs. serum dilution for duplicate samples±SD, as described in Example 6B below for mice immunized with a replication-competent E3 deleted adenovirus (open box) or Adrab.gp (solid box). Native age-matched control mice were used as controls (X). Mice were bled 10 days after immunization and serum antibody titers to adenoviral antigens were determined by an ELISA on plates coated with 1 µg/mL of purified H5.020CMVlacZ virus.
Figure 6B:
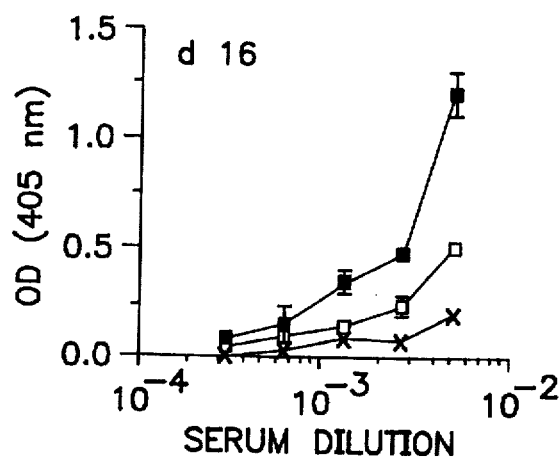
FIG. 6B is a graph similar to that of FIG. 6A for mice immunized as described in FIG. 7A above, and bled at 16 days.

To substantiate this hypothesis, the inventors compared the immune response to rabies proteins upon immunization of mice with a replication-defective E1 deleted adenovirus and a replication-competent adenovirus. Both adenoviruses were of the human strain 5 and both were deleted in E3. These recombinant viruses were tested by enzyme linked immunoadsorbent assay (ELISA) (FIGS. 6A and 6B). The ELISAs were conducted in 96-well microtiter plates coated with 0.1 to 0.2 µg per well of ERA-BPL virus or 1-2 µg per well of purified H5.010CMVlacZ virus, using an alkaline phosphatase conjugated goat anti-mouse Ig as second antibody as described in detail in Xiang and Ertl, *Virus Res.*, 24:297–314 (1992). As shown in FIGS. 6A and 6B, the antibody response to the E1 deleted Adrab.gp virus (solid box) was superior to that of a replication competent Ad virus (open box). This supports the position that long-term expression of viral antigens by a non-lytic virus can induce stronger immune response compared to short-term expression by a replication-competent agent. FIGS. 6A and 6B illustrate that expression of E1 causes a reduction in the antibody response to adenovirus.

These studies demonstrate that the recombinant replication-defective adenovirus used in the present invention shows higher immunogenicity compared to a replication-competent adenovirus. Without wishing to be bound by theory, it is believed that the length of expression of the antigen plays a role in induction of the immune response. In similar studies comparing the replication defective adenovirus vaccine to the VRG vaccine, the Ad vaccine expresses the rabies antigen longer than the VRG recombinant virus vaccine.

EXAMPLE 6

Further Comparative Studies

The following study was performed to test if pre-existing immunity to adenoviral proteins interferes with stimulation of a rabies G protein-specific immune response to the Adrab.gp construct. Groups of C3H/He mice were immunized with $10^5$ or $10^6$ pfu of a replication-competent adenovirus human serotype 5 that had been deleted of the E3 gene. Mice were injected 4 weeks later with $10^6$ pfu of Adrab.gp. Control mice were only injected with Adrab.gp ($10^6$ pfu). Mice were bled 12 days later and neutralizing antibody titers were determined (Table 3).

TABLE 3

The Effect of Pre-Existing Immunity to Adenovirus on the Rabies VNA Response to the Adrab.gp Vaccine

| Pre-immunization Titer | Immunization | VNA |
|---|---|---|
| None | $10^6$ pfu Adrab.gp | 3.645 |
| $10^5$ pfu Ad5d17001 | $10^6$ pfu Adrab.gp | 3.645 |
| $10^6$ pfu Ad517001 | $10^6$ pfu Adrab.gp | 1.215 |
| None | None | <5 |

Figure 7A:
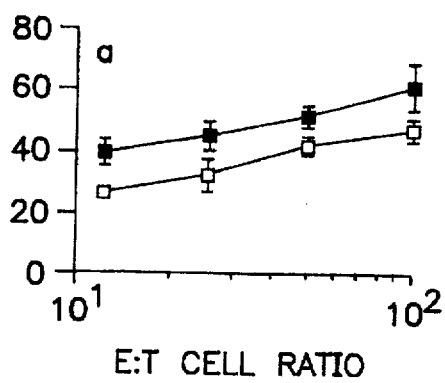
FIG. 7A is a graph plotting mean percentage (%) specific lysis of triplicates±SD vs. E:T cell ratio for C3H/He mice inoculated with $10^6$ pfu of replication competent E3 deleted adenovirus and boosted 3 weeks later with Adrab.gp (open box). Control mice were inoculated with Adrab.gp only (solid box). Mice were sacrificed 4 weeks later and upon restimulation with 1 pfu of Adrab.gp per cell tested on a 4 hour $^{51}$Cr-release assay on L929 cells stably transfected with pSG5rab.gp. See Example 6.
Figure 7B:
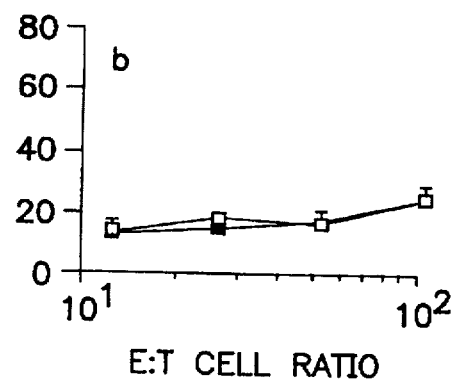
FIG. 7B is a graph similar to FIG. 7A, except the L929 cells were transfected with pSV2neo.

Mice pre-immunized with adenovirus developed VNA to rabies virus upon booster immunization with the Adrab.gp construct. Titers were equivalent, or marginally lower, when compared to those in control mice that had only received Adrab.gp, indicating that antibodies to adenoviruses only marginally inhibit the B cell response to proteins expressed by adenovirus recombinants. Similar data were obtained for the stimulation of cytolytic T cells to rabies virus-infected cells, pre-immune animals showed somewhat lower lysis compared to the control group (see FIGS. 7A and 7B). FIGS. 7A and 7B illustrate that the cytolytic T cell response to rabies virus G protein expressing target cells upon immunization with Adrab.gp is only slightly reduced in animals immune to adenovirus. Nevertheless, adenovirus-immune mice still developed significant T cell responses to the rabies virus G protein upon immunization with Adrab.gp.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

---

What is claimed is:

1. A method of vaccinating a human or animal against rabies comprising administering to said human or animal a single dose of an effective amount of a recombinant adenovirus comprising an adenovirus containing a complete deletion of its E1 gene and at least a functional deletion of its E3 gene, and, in the site of the E1 gene deletion, a sequence comprising a cytomegalovirus promoter directing the expression of DNA encoding a rabies virus protein, which, when administered to the animal or human in said recombinant virus, elicits a protective immune response against rabies virus.

2. The method according to claim 1, wherein the protein is rabies virus G glycoprotein.

3. The method according to claim 2, wherein the rabies virus protein is derived from the Evelyn Rockitniki Abelseth rabies strain.

4. The method according to claim 1, wherein a single dose of between $10^4$ and $10^7$ pfu of the adenovirus are administered to the animal.

5. The method according to claim 1, wherein the adenovirus is administered subcutaneously, rectally, intratracheally, intramuscularly or intranasally.

6. The method according to claim 1, wherein said adenovirus is Adrab.gp ATCC Accession No. VR-2554.

7. A method of preventing rabies infection in an animal comprising administering to the animal a single dose of an effective amount of the recombinant replication-defective Adrab.gp adenovirus ATCC Accession No. VR-2554.

8. The method according to claim 7, wherein a single dose of between $10^4$ and $10^7$ pfu of the virus are administered to the animal.

9. The method according to claim 7, wherein the virus is administered subcutaneously, intratracheally, intramuscularly or intranasally.

10. A vaccine composition comprising:

between $10^4$ and $10^7$ pfu of a recombinant adenovirus containing a complete deletion of its E1 gene and at least a functional deletion of its E3 gene, and in the site of the E1 deletion a sequence comprising a cytomegalovirus promoter directing the expression of DNA encoding a rabies virus G protein, which, when administered to the animal or human in said recombinant virus elicits a protective immune response against rabies virus in a single dose of an unexpectedly low vaccine dosage.

11. The vaccine composition according to claim 10 comprising Adrab.gp ATCC Accession No. VR-2554.

* * * * *